Figure 1:
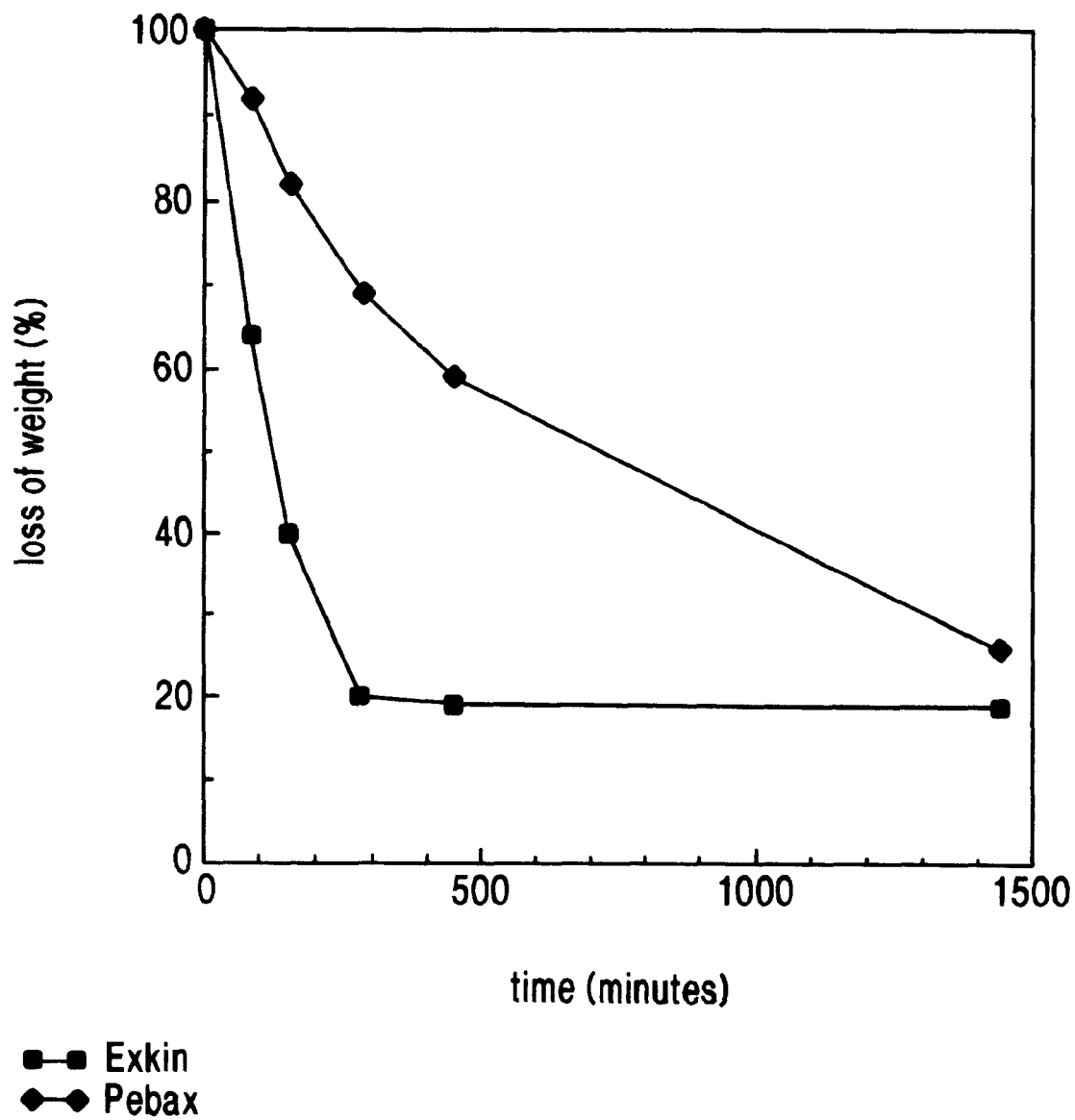

United States Patent [19]
Schacht et al.

[11] Patent Number: 6,132,759
[45] Date of Patent: Oct. 17, 2000

[54] MEDICAMENTS CONTAINING GELATIN CROSS-LINKED WITH OXIDIZED POLYSACCHARIDES

[75] Inventors: Etienne Schacht, Staden; Jean Pierre Draye, Chaste; Bernard Delaey, Zingem, all of Belgium

[73] Assignee: Innogenetics N.V., Belgium

[21] Appl. No.: 09/180,057

[22] PCT Filed: May 5, 1997

[86] PCT No.: PCT/EP97/02279

§ 371 Date: Oct. 27, 1998

§ 102(e) Date: Oct. 27, 1998

[87] PCT Pub. No.: WO97/41899

PCT Pub. Date: Nov. 13, 1997

[30]  Foreign Application Priority Data

May 3, 1996 [EP] European Pat. Off. .............. 96870059

[51] Int. Cl.[7] .............................. A61L 15/32; A61K 9/50
[52] U.S. Cl. ..................... 424/445; 424/449; 424/488; 424/499
[58] Field of Search ............................................. 424/445

[56]  References Cited

U.S. PATENT DOCUMENTS 5,041,292  8/1991  Feijen et al. ............................ 424/484
5,676,967  10/1997 Williams et al. ........................ 424/445
5,783,214  7/1998  Royer ..................................... 424/499

FOREIGN PATENT DOCUMENTS 822075  9/1969  Canada .

*Primary Examiner*—Peter F. Kulkosky
*Attorney, Agent, or Firm*—Bierman, Muserlian and Lucas

[57]  ABSTRACT

The present invention relates to a wound dressing comprising a biopolymer matrix comprising gelatin cross-linked with an oxidized polysaccharide. Preferably said oxidized polysaccharide comprises an oxidized dextran or an oxidized xanthan. Preferably said matrix is in the form of a hydrated film, a hydrated or dry foam, dry fibers which may be fabricated into a woven or non-woven tissue, hydrated or dry microbeads, dry powder; or said matrix is covered with a semipermeable film, so as to control the humidity of the wound covered with the dressing, with the permeability chosen so as to maintain this humidity within a therapeutically optimal window. A polysulfated polysaccharide with a M.W. greater than 30,000 kDa is mechanically entrapped during the formation of said matrix.

17 Claims, 15 Drawing Sheets

MEDICAMENTS CONTAINING GELATIN CROSS-LINKED WITH OXIDIZED POLYSACCHARIDES

This application is a 371 of PCT/EP97/002279 filed May 5, 1997.

The present invention relates to a medicament containing a biopolymer matrix comprising gelatin cross linked with oxidized polysaccharides. The material is useful for the covering of a variety of wound types, particularly chronic wounds and burns. The material is also suitable for the controlled release of drugs. When loaded with suitable growth factors or wound repair promoting substances, the matrix is useful for the fabrication of wound dressings for the treatment of a variety of wound types, particularly chronic wounds and burns.

A very large number of people are suffering from chronic non-healing skin wounds. Worldwide, 8 million people have chronic leg ulcers and 7 million people have pressure sores (Clinica 559, 14–17, 1993). In the US alone, the prevalence of skin ulcers is 4.5 million, including 2 million pressure sore patients, 900,000 venous ulcer patients and 1.6 million diabetic ulcer patients (Med Pro Month, June 1992, 91–94). The cost involved in treating these wounds is staggering and, at an average of $3,000 per patient, reaches over $13 billion per year for the US alone. Burn wounds have a reported incidence of 7.8 million cases per year worldwide, 0.8 million of which need hospitalisation (Clinica 559). In the US there are 2.5 million burn patients per year, 100,000 of which need hospitalization and 20,000 of which have burns involving more than 20% of the total body surface area (MedPro Month, June 1992).

A common feature in the treatment of these wounds is that they need covering for optimal healing. The beneficial effect of covering wounds is situated at different levels and is dependent on the type of dressing material used. First, especially with acute wounds, suitable dressings may help to achieve haemostasis and thus control blood loss. Secondly, covering effectively shields the wound from the environment, thus protecting it from microbial contamination. Furthermore, some so-called occlusive or semi-occlusive wound dressings have the capability of maintaining the wound moist, which is beneficial for healing. Finally, some wound dressings may themselves directly promote the healing process, for instance because they contain components which directly promote cell growth or migration or which attract or activate cells from the immune system which on their turn secrete growth-promoting substances. Other dressings may contain antimicrobial substances, which are helpful to control infection of the wound.

Over time, a surprisingly wide variety of dressing materials have been used for wound covering, many of which are currently commercially available. Each of them has its own indications, dependent on wound type, depth, size, absence or presence of infection, level of exudate formation, etc.

Cotton gauze, for instance, is widely used as wound dressing. It has the advantage of being cheap, but the disadvantage of being not occlusive and sometimes becoming encrusted into the wound. To prevent this, these dressings are sometimes impregnated with a greasy substance, such as paraffin. A commercially available example of such a dressing is Jelonet™ (Smith and Nephew, UK).

Another class of wound dressings are the absorptive hydrogel dressings. These have no occlusive properties, but have a high capacity for the absorption of exudate and slough. They consist of hydrophilic polymers such as gelatin, polysaccharides, polyacrylamide, etc. which swell upon contact with wound fluid and can absorb several times their own weight of exudate. Commercially available hydrogel dressings include Intrasite gel (Smith and Nephew, UK) and Vigilon (CR Bard, USA). A special type of hydrogels are the alginates, which are hydrophilic polysaccharides extracted from seaweed. They are produced as thin nonwoven tissues or as ropes. Upon contact with the wound fluid, they turn into a gel which has a high absorptive capacity for wound fluid. Examples include Kaltostat (Brit-Cair, UK) and Sorbsan (Steriseal, UK).

Another type of dressings are the occlusive or semi-occlusive dressings. In their simplest form, they usually exist of a thin, flexible plastic membrane, e.g. from polyurethane. To facilitate application, these dressings are usually fabricated with a self-adhesive coating. These dressings are called occlusive because they limit water evaporation from the wound surface, thus keeping it moist. Examples of such dressings are Opsite (Smith and Nephew, UK) and Tegaderm (3M, USA). Examples of semi-occlusive dressings are Omiderm (Iatro Medical Systems, UK) and Exkin (Koninklijke Utermöhlen, The Netherlands). The latter dressings allow a slightly higher evaporation rate, resulting in a semi-dry wound surface.

A more complex type of occlusive dressings are the hydrocolloid (HCD) dressings. These are made up of hydrocolloid particles (e.g. consisting of gelatin, pectin, etc.) embedded in a hydrophobic matrix (e.g. a polyisobutylene). These dressings may be backed with an occlusive membrane and/or a foam plastic layer. In addition to being occlusive, HCD dressings have a high absorptive capacity, making them very suitable for the treatment of wounds producing high amounts of exudate. These beneficial properties have made HCD dressings among the most successfully used dressings for the treatment of chronic ulcerations of the skin. Commercially available examples of these dressings include Duoderm° (Convatec, UK) and Tegasorb™ (3M, USA).

Although highly successful, recent reports suggest that HCD dressings may nevertheless induce undesirable side reactions in the treated tissues. For example, Van Luyn reports that Duoderm E (Convatec, UK), Biofilm (Biotrol SPA, France), Comfeel (Coloplast, Denmark) and Ulcer dressing (Johnson and Johnson, USA), all of which are HCD dressings, fall within the high toxicity class when tested in a methylcellulose assays using human skin fibroblasts as target cells (Van Luyn, M. Doctoral Thesis, 1992, State University Groningen, The Netherlands; Van Luyn, M., Abstract Book of the joint WHS/ETRS meeting, Amsterdam, 1993 p114). All the HCD dressings tested by this author highly inhibited cell growth (>70%) and induced strongly deviant morphologies in the surviving cells. Leek et al. (Abstract Book of the Second Annual WHS Meeting, Richmond, Va., USA, p75, 1992) have tested four HCD dressings in full-thickness excisional wounds in pigs. All dressings induced development of granulomatous lesions between 4 and 10 days post wounding and exhibiting little evidence of resolution at 3 months post wounding. The most severe reaction was obtained with Duoderm and Intrasite HCD. Rosdy and Clauss (J. Biomedical Mat. Res. 24, 363–3777, 1990) found that the HCD dressing Granuflex™ (Bristol-Myers Squibb, USA) induced cytopathic effects on MRC5 fibroblasts and epidermal cells upon direct contact. Young et al. (J. Invest. Dermatol. 97, 586–592, 1991) describe in an animal model system the development of deep-seated foreign body type reactions and granulomata in healed wounds which were treated with HCD dressings. Our own experiments with the HCD dressing Duoderm™ show that this dressing results in a marked and chronic inflammatory response when placed in full thickness wounds in pigs.

The above mentioned data suggest that, while HCD dressings may promote wound healing in the short term, their use is often associated with undesirable inflammatory effects. Therefore, it is clear that there is a need for a wound dressing displaying the beneficial properties of HCD dressings, yet resulting in substantially less chronic inflammation or foreign body response. Such a wound dressing would stimulate granulation tissue formation, be absorptive and preferably be biodegradable within a limited time frame.

Gelatin, which is a denatured form of the protein collagen, has been used in a variety of wound dressings. Since gelatin gels have a relatively low melting point, they are not very stable at body temperature. Therefore, it is imperative to stabilize these gels by establishing cross-links between the protein chains. In practice, this is usually obtained by treating the gelatin with glutaraldehyde or formaldehyde. Thus cross-linked gelatin may be fabricated into dry sponges which are useful for inducing haemostasis in bleeding wounds. Commercially available examples of such sponges include Spongostan° (Ferrosan, Denmark) and Gelfoam (Upjohn, USA). A major disadvantage of these sponges is that the cross-linking agent used (formaldehyde or glutaraldehyde) is toxic for cells. The negative effect of glutaraldehyde cross-linking is exemplified, for instance, by the findings of de Vries et al (Abstract Book of the Second Annual Meeting of the WHS, Richmond, USA, p51, 1992). These authors showed that glutaraldehyde cross-linked collagen lattices were toxic for cells, whereas the non cross-linked variety was not. Therefore, despite their beneficial haemostatic properties, these products are not very optimal as wound dressings for the treatment of problematic wounds such as chronic ulcers or burns. Consequently, a gelatin-based wound dressing which uses a different, less toxic, cross-linking technology would be very desirable. Dextran is a polysaccharides which is also widely used for medical purposes, and which may also be used in a wound dressing. For example, PCT publication number WO 94/27647 (Smith and Chakravarty) teaches the fabrication of a polymer composition comprised of cross-linked dextran, where the cross-linking groups consist of linear imido carbonate or carbonate groups. This polymer can be incorporated in a wound dressing. An important feature of this polymer composition is that it is hydrolytically labile. This means that hydrated forms of the material are inherently unstable, and that the polymer can only be stored for prolonged periods when dehydrated.

Schacht et al., in European patent published under N° 0308330 disclose a polymer composition comprising gelatin, cross-linked with oxidized polysaccharides onto which proteins, enzymes or micro-organisms are additionally immobilized.

Apart from the development of improved dressings, increasing attention has been given over the last years to the possible use of growth factors to promote the healing of wounds, in particular burns and ulcers. Following are but a few of the scientific reports describing the use of growth factors for promoting wound healing in humans. Epidermal Growth Factor (EGF) has been used for the treatment of skin graft donor sites (Brown et al., N. Engl. J. Med. 321, p76–79, 1989) and chronic ulcers (Brown et al., Plast. Reconstr. Surg. 88, p.189–194, 1991). This same factor has also successfully been used in ophthalmology for the topical treatment of traumatic corneal ulcers (Scardovi et al., Opthalmologica 206, p.119–124, 1993) and to promote endothelial wound healing in human corneas (Hoppenreijs et a., Invest. Ophtalmol. Vis. Sci. 33, p1946–1957, 1992). EGF eye drops are commercially available under the trade name Gentel° from Inpharzam S.A. (Cadempino, Switzerland). Basic Fibroblast Growth Factor (bFGF) has been used for the treatment of chronic pressure sores (Robson et al., Ann. Surg. 216, p.401–408, 1992) and for the treatment of experimentally induced suction blisters in humans (Lyonnet et al., J; Invest. Dermatol. 96, p.1022, 1991). Transforming Growth Factor $\beta$ (TGF$\beta$) was found to have beneficial effects in the treatment of full thickness macular holes in human eyes (Glaser et al., Ophthalmology 99,n p1162–1173). Platelet Derived Growth Factor (PDGF) was found to be a wound healing stimulator of chronic pressure ulcers in humans (Robson et al., Lancet 339, p.23–25, 1992). Human Growth Hormone has been reported to accelerate wound healing in children with large cutaneous burns (Gilpin et al., Ann. Surg. 220, p.19–24, 1994). Platelet lysate, which is a crude preparation containing a mixture of several growth factors, has also been found to stimulate the healing of chronic ulcers (Knighton et al., Surgery Gyn. Obst. 170, 56–60, 1990). The latter preparation has been commercialized under the trade name Procuren by Curative Technologies, Inc (USA). Our own studies with crude keratinocyte lysates, which also contain several cell growth promoting activities, have shown an increase of the healing speed of burns wounds and an enhancement of epithelialisation of middle ear defects in chronic otorrhea patients and after tympanoplasty.

One common problem with all aforementioned studies is to find an efficient way for the controlled delivery of the active substances to the wound. In most cases; these substances are simply applied as an aqueous solution, or at best as a formulation in a semi-liquid gel or cream. Using such formulations, most of the active substance is released in the wound site very rapidly. Nevertheless, it is known that many growth factors are relatively unstable and it is expected that their half life in the wound environment is relatively short. This means that there is a need for a device which would allow the controlled release of the active substance over a prolonged period, at the same time protecting the still unreleased factor from premature degradation. This would significantly lower the cost and increase the efficiency of growth factor wound therapy by reducing the necessary dose and by securing a more prolonged effect of the active substance, thereby reducing the number of applications. Several strategies and materials have been considered for the controlled release of peptide growth factors and similar substances. Following are a few of the approaches which have been reported in the scientific literature or for which patent applications have been filed.

One class of controlled release devices consists of synthetic biodegradable polymers. For instance, poly-lactide-glycolides (PLG) are hydrolytically degradable polymers which can be used for the slow release of variable pharmaceutical substances including bioactive macromolecules such as calcitonin, LHRH, somatostatin, insulin, interferon and vaccines (Lewis, Pharmaceutical manufacturing International, 1993, p99–105). Due to the use of organic solvents, incorporation of biologically active peptides or proteins into PLG often results in their inactivation. Although this can be circumvented by the production of physical PLG/peptide mixtures (e.g. by compression moulding of powder mixes), these may be less suitable as wound dressings because of their rigidity and brittleness.

Apart from synthetic polymers, a wide variety of naturally occurring polymers, or modifications thereof, have been used for controlled release of bioactive peptide factors. An example of this is methylpyrrolidone chitosan fleeces loaded with bFGF (Berscht et al., Biomaterials 15, 593–600, 1994). A particular controlled release composition is disclosed in WO 92/09301 by Greisler, which teaches the use of growth factor-containing fibrin tissue sealant for acceleration of wound healing. Products according to the latter invention would probably be relatively expensive, due to the high cost of commercially available fibrin glues adhesives.

A frequently used biopolymer for controlled release is also gelatin. Collagen-containing gelatin sponges for protein drug delivery have been disclosed in patent applications EP 0568334 and WO 93/21908. Golumbek et al., in Cancer Res. 53, p5841–5844 (1993), describe the use of gelatin microspheres loaded with IFNγ or GM-CSF as potential cancer therapy vaccines. Cortesi et al. (Int. J. Pharm. 105, p.181–186, 1994) describe the use of gelatin microspheres for the release of synthetic oligonucleotides and PCR-generated DNA fragments. The synthesis of gelatin microspheres containing Interferon was reported by Tabata and Ikada (Pharm. Res. 6, p.422–427, 1989). Shinde and Erhan (Bio-Med. Mat. Eng. 2, p.127–131, 1992) describe flexibilized gelatin films for the release of insulin.

As discussed above, the commonly used glutaraldehyde or formaldehyde for cross-linking these gelatin-based biomaterials have the disadvantage of being toxic for the cells. In addition to their toxic properties, glutaraldehyde and formaldehyde are also expected to affect the biological activity of incorporated bioactive protein substances when cross-linking is carried out after addition of these substances to the system. Consequently, a gelatin-based slow release device which uses a different, less toxic, cross-linking technology would be very desirable for the fabrication of, for instance, growth factor-medicated wound dressings.

The present invention thus aims at providing a suitable wound dressing.

The present invention also aims at providing a suitable slow or controlled release device.

The present invention further aims at methods for producing and using said wound dressings or said controlled or slow release devices.

The present invention relates to the unexpected finding that polymers comprising gelatin cross-linked with oxidized polysaccharides constitute excellent medicament such as dressings for the treatment of wounds. The cross links are formed by Schiff base formation between free amino groups of the gelatin and aldehyde groups in the polysaccharides. A polysaccharides particularly suited for use in the present invention is dextran. For the purpose of clarity, oxidized dextran shall be called "dextranox" hereafter, and the polymer composition consisting of gelatin, cross-linked with oxidized polysaccharides (in particular dextran), shall be called "GDP" (for Gelatin-Dextranox Polymer).

One of the advantages of the presently disclosed medical composition for wound healing purposes is that it is a fully biodegradable material. Nevertheless, since biodegradability is not obtained through the use of hydrolytically cleavable bonds, the object of our invention is sufficiently stable in a hydrated form to allow prolonged storage. Unlike non cross-linked gelatin it also has a melting point sufficiently high to remain on the wound site in an intact form for a sufficiently long time. Another advantage is that the disclosed wound dressing has substantially reduced cytotoxical and inflammatory properties as compared with existing gelatin-based materials. This is exemplified in examples 3–5. Yet another advantage is that the material induces granulation tissue formation in experimental wounds, a feature which is highly desirable for the treatment of chronic wounds. A further advantage is that one of the embodiments of the disclosed dressing offers the possibility to immobilize sulfated dextrans or similar poly-anionic molecules into the dressing, a modification which enhances the binding of incorporated or local heparin binding wound repair modulating factors.

According to a further aspect, the present invention relates to the unexpected finding that gelatin cross-linked with oxidized polysaccharides constitutes an ideal biopolymer matrix for the incorporation and subsequent controlled release of bioactive peptide factors. Contrary to the anticipations, it was discovered that the incorporated bioactive peptide factors were only marginally, cross-linked to dialdehyde groups of the oxidized polysaccharides. Therefore, pharmaceutically active peptides can be incorporated in the matrix by mixing them with the solubilized gelatin component, followed by addition of the dextranox component to obtain a.stabilized cross-linked gel containing the peptide in a releasable form. This allows a much more elegant, cheaper and controllable production process as compared with the alternative procedure of incorporating the peptides by a sorption process (e.g. by soaking the dehydrated or partially dehydrated matrix in a solution containing the peptide). Such medicated GDP matrices may be used for several therapeutical applications, in particular for the fabrication of medicated wound dressings, e.g. by loading them with growth factors or other wound repair-enhancing substances.

The GDP matrix also functions as an efficient matrix for the controlled release of biomolecules, as shown in examples 6–8. Medicated GDP matrices prepared in this way are useful for a variety of therapeutical applications, in particular for the fabrication of medicated wound dressings.

The term "biopolymer matrix" according to the present invention refers to a matrix composed of mixtures of gelatin and oxidized polysaccharides as defined above having as a basic property that they are biodegradable.

In a preferred embodiment, the proposed wound dressing consists of a hydrated sheet or film of matrix as defined above, backed with an occlusive or semi-occlusive film. Occlusive in this context means that the film has a permeability for water which is sufficiently low to prevent desiccation of the wound, yet sufficiently high to prevent excessive accumulation of exudate below the wound dressing.

In another embodiment, the wound dressing is fabricated in the form of dehydrated microparticles. These microparticles are especially suited to be applied into deep, highly exudative wounds. By virtue of the high fluid-absorptive capacity of the particles, the wounds may in this way be cleaned from excess exudate and slough.

In yet another form, the proposed polymer is fabricated into a flexible dehydrated foam. Such a foam may be easily applied onto shallow wounds and also has a high absorptive capacity.

The proposed polymer can also be used for the fabrication of a wound dressing containing one or more wound repair-promoting substances. Examples of such substances are for instance growth factors such as EGF, TGF-α, FGFs, PDGFs, amphiregulin, HB-EGF, betacellulin, TGF-β, IGFs or other mitogens or their antagonists which may modulate the wound repair process. Such a medicated wound dressing can be produced in different forms, including flexible sheets, foams, microparticles, fibers to make up woven or non-woven tissues, etc. One of the embodiments of the invention concerns the production of a wound dressing containing multiple layers, where each layer contains a different active component, so as to achieve a programmed delivery of the different components over time. In another embodiment, suitable affinity groups are incorporated into the polymer matrix, to increase the affinity of the matrix for the incorporated active substances, thus decreasing their release rate and/or to protect them from premature degradation or inactivation. Examples of such affinity groups include heparin or functional analogs of heparin such as dextran sulfate, which have an affinity for heparin binding growth factors such as the FGFs, amphiregulin and HB-EGF. Possible affinity groups also include monoclonal or polyclonal antibodies or microproteins as obtained through phage display, and which have a high and selective affinity for specific growth factors.

The present invention relates more particularly to the finding that GDP constitutes an excellent material for the preparation of dressings suitable for the covering and treatment of wounds. In addition, the material also displays unexpectedly favourable controlled release properties for the delivery of therapeutic substances, particularly to wounds. GDP is prepared by the cross-linking of solubilized gelatin with oxidized dextran. Gelatin is a denatured form of the connective tissue protein collagen. Several types of gelatin exist, depending on the source of collagen used, and on the extraction and production process employed. One type of gelatin is extracted from animal bones, while another type is extracted from animal skin. Usually, the animal material is from bovine or porcine origin. Depending on the extraction process, two types of gelatin can be prepared: the A (or acidic) type, which is prepared by acid hydrolysis of the collagen and which has an isoelectric point of about 8, and the B (or basic) type, which is prepared by basic hydrolysis of the collagen and which has an isoelectric point of about 5. Both types of gelatin are useful for preparation of GDP or matrices as defined above suitable for the present invention. However, because cross-linking with dextranox is preferably performed at a pH superior to the isoelectric point of the gelatin, the A type is the most preferred type of gelatin, because it allows cross-linking at an approximately neutral pH of between 6 and 8. An important property of gelatin is that it forms gels with a certain rigidity. The rigidity of these gels is expressed by the Bloom number of the gelatin. For the purpose of this invention, gelatins with a variety of Bloom numbers are usable. However, Bloom numbers of at least 150, preferably at least 200, more preferably at least 250 are preferred because they offer GDP of a high mechanical strength which can easily be fabricated in films or sheets. Again, since gelatins of the A type usually have higher Bloom numbers, this type is the most preferred within the framework of this invention.

The oxidized polysaccharides used in the present invention is preferably an oxidized dextran. However, it shall be obvious to the person skilled in the art that other polysaccharides with suitable viscosity, molecular mass and oxidation properties can also be used, as described in the above-mentioned patent application EP 0308330 by Schacht and Nobels, the contents of which are hereby incorporated by reference. An example of such another polysaccharide is oxidized xanthan. Although different polysaccharides are thus conceivable for the purpose of this invention, we shall from hereon only refer to the use of oxidized dextrans (which we call dextranox). This is simply for the sake of clarity and should in no way be considered as a limitation with respect to the range of possible polysaccharides useful within the framework of the invention. The molecular weight of the dextran used for the fabrication of wound dressings according to the invention is preferably below 5,000,000, more preferably between 10,000 and 100,000, in such a way that the viscosity of the aqueous solution of the dextran is not too high, for example between 0.1 and 1 Pa.s for a 2% solution (as measured using a Brookfield LVT viscosimeter operated at 30 cycles).

Oxidation of dextran is a well-known reaction. For instance, oxidation can be conveniently obtained by treatment with an aqueous solution of a salt of periodic acid, such as sodium periodate. The purpose of the oxidation is to create the formation of reactive dialdehyde residues in the polysaccharides. Although the oxidation procedure described above is preferred, it shall be clear to the person skilled in the art that other oxidation methods leading to the formation of dialdehyde residues are also possible, for instance, by treatment with periodic acid or lead tetra acetate in an organic solvent such as dimethylsulfoxide. After oxidation, the dextranox can be conveniently purified and separated from low molecular weight reaction components by classical purification methods. Examples to accomplish this include, but are not limited to: precipitation (for instance by addition of acetone, methanol or isopropanol) or dialysis, ultrafiltration or gel permeation chromatography, followed by lyophilisation.

Cross-linking between gelatin and dextranox is accomplished by the formation of so-called Schiff base links between free amino groups present on the gelatin (notably on the lysine residues thereof) and the dialdehyde residues on the dextranox. This reaction is performed in aqueous medium and the speed and degree of cross-linking are dependent on a variety of parameters, such as the type of gelatin, the concentration, degree of dialdehyde substitution and molecular weight of the dextranox, the pH, buffer type and the presence of electrolytes in the reaction medium, etc. Suitable reaction parameters are described for instance in patent application N° EP 0308330, cited above. For the purpose of this invention, the percentage of oxidation of the dextranox is preferably between 5% and 50%. For application of GDP as a slow release device for the delivery of proteins, it is preferably between 5% and 20%, more preferably between 5 and 15%, even more preferably between 7 and 12%. The concentrations of gelatin and dextranox are preferably between about 2% and about 20%, more preferably between 5 and 15%, even more preferably between 7 and 12%.

According to the present invention, GDP prepared as described above can be used for the fabrication of a variety of wound dressings.

According to a preferred embodiment, GDP is fabricated into a thin sheet or film, suitable for application onto a wound surface. There exist several known technologies to accomplish this. For instance, a solution of gelatin (kept at a temperature higher then the gelification point of the gelatin used, usually >30° C.) can be mixed with a solution of dextranox and be poured into a suitable cast before any appreciable cross linking takes place. After the cross-linking process is finished, the film can be removed from the cast. Another way to form films is to use one of the processes utilized in the photographic industry for the preparation of photographic films and papers. For the purpose of this invention, the thickness of the films shall preferably range between 0.1 and 2 mm, more preferably between 0.3 and 1 mm, although differently sized films may be appropriate for some applications.

When a film according to the procedure described above is placed onto a wound for a prolonged period, it is possible that dehydration still takes place because fluid can evaporate from the surface of the film. To prevent this, the GDP wound dressing film can be additionally covered by one of the commercially available occlusive or semi-occlusive wound dressing films, for example a polyurethane such as Opsite or Tegaderm. However, a better solution is provided according to another preferred embodiment of the present invention where a GDP film is directly laminated onto a suitable occlusive membrane during the production process. Examples of such membranes are provided in example 2. For instance, particularly well suited plastic films are those from the Pebax series, such as Pebax 1205, which are produced by Elf. This type of film has a very low water vapour permeability, making it very suitable for the fabrication of wound dressings intended for use on relatively dry wounds. For application on more exudative wounds a higher evaporation rate is desirable, to prevent excessive accumulation of fluid under the dressing. In this instance, a backing membrane with higher water vapour permeability may be preferred, such as those manufactured by Utermöhlen in The Netherlands (Exkin) or by Iatro Medical Systems in the UK (Omiderm). To the person skilled in the art it shall be obvious that, depending on the type of wound, the degree of exudate formation and the desired frequency of dressing change, other backing films with different water vapour permeability properties can be used, to obtain an optimal fluid balance at the wound surface.

According to another embodiment, GDP is fabricated into a hydrated or dehydrated particulate wound dressing. Several techniques are known to achieve this. A dry GDP powder or granulate may be produced by dehydration of a solid GDP mass after cross linking, followed by powdering the dehydrated material. Dehydration may be obtained for instance by drying in a stream of dry air, lyophilisation, organic solvent extraction, etc. After the powdering or granulation step, particles of a desired size may be selected, for instance by sieving through a series of sieves with a suitable mesh size. For the manufacturing of spherical or substantially spherical GDP particles, one can generate a spray by pushing a freshly prepared gelatin/dextranox mixture through an approporiate atomization nozzle. It has to be understood that the sizes of the spray drops will vary according to the type of application and can be determined by choosing the appropriate nozzle type, pressure and capacity for the atomization process. Another possibility is to emulsify a freshly prepared gelatin/dextranox solution with a non-water miscible solvent such as an aliphatic or aromatic hydrocarbon or an oil, provided this solvent does not contain any residues which can react with aldehydes. To create spherical particles of a larger size, the gelatin/dextranox solution may alternatively be added dropwise to the non-water miscible solvent. Other techniques to produce hydrated or dehydrated gel particles, known to the person skilled in the art, may also be used to prepare a particulate wound dressing according to this invention. Such a particulate wound dressing may be useful for the treatment of a variety of wound types, but especially for the treatment of relatively deep and highly exudative wounds, such as some chronic ulcers or diabetic foot ulcers or decubitus wounds. When applied in a dehydrated form they have the property of absorbing exudate. This is a highly desirable feature, since removal of excess exudate and slough is an important therapeutical goal with respect to the prevention of microbial colonization, to the limitation of further necrotization and to the relieve of discomfort for the patient. Such a particulate wound dressing can also be used in its hydrated form (i.e. by omitting the dehydration process after particle preparation or by rehydrating dehydrated particles before application onto the wound). In this latter form, it can be applied for instance as a paste to wounds which produce less exudate. It shall be obvious that, depending on the needs of a particular wound type, the possibility also exists to use the particulate wound dressing in a partially hydrated form. In the latter form, the dressing still would have substantial fluid absorptive properties, yet, by virtue of a certain stickiness, it would easily be applicable as a paste or be fabricated into a thin film. By adapting the type of gel, wound dressings can be designed that are appropriate for treatment of other wounds such as corneal wounds or defects, tympanic membrane reconstructions, or other middle ear reconstructions, or chronic otorrhea. It shall also be clear that the dehydrated, partially hydrated and fully hydrated forms of these particulate wound dressings can be suspended in any suitable aqueous or organic excipient to facilitate application. Examples of such excipients include, but are not limited to: paraffin oil, vaseline, glycerol, etc.

Another physical form into which GDP wound dressings can be fabricated is a foam. This can be achieved for instance by adding a suitable biocompatible detergent to the freshly prepared gelatin/dextranox mixture, followed by introducing small gas bubbles into the mixture. The gas can be air, nitrogen, helium or another gas, preferably a gas which is not water soluble, non-toxic and chemically inert. Other techniques known in the art for producing foams are also suitable, provided they do not result in the introduction of non-biocompatible components or do not interfere with the cross-linking process. Foams can be used either in the hydrated form, or be also partially or completely dehydrated. They can be produced as sheets, rods, plugs, pads, etc., or in any other form which is considered suitable for easy application to a wound site.

In a further embodiment, other molecular components may be covalently attached to or into the GDP matrix through SIPN technology (semi-interpenetrating polymer network) or a combinatiuon of both. Especially, high molecular weight components can be mechanically entrapped within the polymer meshwork, such that through covalent attachment is not always required. These components may consist of molecules which have a known affinity for certain growth factors or wound healing-promoting substances. Examples of such components are those with affinity for heparin binding proteins, such as heparin or functional analogs of heparin such as heparan sulfate, chondroitin sulfate, dermatan sulfate, dextran sulfate or any other non-toxic polyanionic group displaying sufficient affinity for one or more of the molecular factors implicated in the wound healing process or components such as monoclonal or polyclonal antibodies or microproteins that can be obtained through phage display that have a high and selective affinity for molecular factors implicated in the wound healing process. When applied onto a wound, such affinity GDP matrices have the potential to act as a reservoir for the accumulation and stabilisation of locally available endogenous growth factors or other wound repair stimulating factors. These factors may subsequently be gradually released, thus promoting healing of the injury. The potential of heparin-like molecules and similar polyanions to bind and stabilize certain growth factors is well known in the art. The following are but a few examples from the scientific literature discussing this subject. Volkin et al. have described the physical stabilisation of acidic FGF by different types of polyanions (Arch. Biochem. Biophys., 300, p.30–41, 1993; Biochim. Biophys. Acta 1203, p.18–26, 1993). Tomoko et al. describe the stabilization of basic FGF with dextran sulfate (FEBS Letters, 306, p.243–246, 1992). Turnbull and Gallagher review the role of heparan sulphate as a functional modulator of fibroblast growth factor activity (Biochem. Soc. Trans. 21, 477–482, 1993). By the incorporation of such polyanionic compounds in the GDP matrix of this invention, the favourable biocompatibility and wound healing properties of the matrix may still further be improved.

Alternatively the components incorporated into or attached to the affinity matrix, may display an affinity for molecular factors that is high enough that binding can become a stable process. When applied onto a wound, such affinity GDP matrices have the potential to specifically sequester molecular factors that are detrimental to the wound healing process, such as factors that cause deregulated growth or hypertrophy or a superfluous formation of collagen, and that can cause the formation of keloids.

In the present invention we also disclose our discovery that GDP constitutes an efficient and versatile material for the fabrication of slow or controlled release devices for the delivery of pharmacologically active substances. It was an unexpected finding that also peptide or polypeptide substances can be incorporated and subsequently efficiently released from GDP matrices. This was surprising considering the fact that most peptides have free amino groups which can react with the aldehydes of the dextranox. One would therefore expect that these peptides would be irreversibly cross-linked to the GDP matrix, preventing their release. This is however not the case, as is demonstrated in examples 6–8, showing the efficient release of an oligopeptide, iodinated IL-1$\alpha$, TNF-$\alpha$, IL-8, BSA and bioactive EGF. A possible explanation for this behaviour is that the available aldehyde residues on the dextran are out-titrated preferentially by the amino groups of the gelatin, which is present in an about 10,000-fold higher concentration (100 mg/ml) than the incorporated factors (present at about 10 $\mu$g/ml).

Pharmacologically active factors of interest can be incorporated in GDP matrices in several ways. The most preferred method is to add the factors prior to the cross linking process. Therefore, an aqueous solution of the active agent is mixed with an aqueous solution of gelatin at a temperature of about 37° C., followed by mixing this solution with an aqueous solution of dextranox. The resulting mixture is allowed to cool, during which time the gelatin sets and cross linking between gelatin and dextranox chains takes place. Since gelatin solutions are viscous, care should be taken that the different components are mixed thoroughly, so that a homogeneous distribution of the active agent in the GDP matrix is obtained. Another possibility is to incorporate the active factors in the GDP matrix after the cross linking process is completed, by means of a sorption procedure. Therefore, the GDP matrix is partially or completely dehydrated. This dehydration can be achieved by drying the matrix in an air stream, by lyophilisation, by organic solvent extraction or by any other suitable means resulting in removal of water from the matrix. Subsequently, the dehydrated matrix is soaked in an aqueous solution containing the active, agent. During this soaking process, the matrix is rehydrated, at the same time absorbing part of the active agent.

One of the possible applications of the present invention lies in the fabrication of wound dressings containing one or more wound repair stimulating factors and/or a suitable antiseptic agent. Wound repair stimulating agents which are eligible for incorporation in such a wound dressing are for instance growth factors such as those belonging to the class of the EGF, FGF, PDGF, TGF-$\beta$, VEGF, PD-ECGF or IGF families. Another suitable agent would be a releasate from human platelets, which is for instance marketed by Curative Technologies Inc under the name Procuren. Also possible would be the incorporation of a conditioned medium, a lysate or an extract prepared from keratinocytes, such as disclosed in patent applications U.S. Ser. No. 9,106,161 (Oregon Univ.), EP88101576 (Eisinger), WO93/10217 (IG). Suitable antiseptic agents include antibiotics, antibacterial sulfamides or peptides, chinolones, antimycotics, etc., as far as they are suitable for topical use. Wound dressings containing wound repair promoting agents can be used for the treatment of wounds which are difficult to heal. Injuries which are eligible for such treatment include but are not limited to chronic ulcera, corneal injuries, tympanic membrane perforations, surgical wounds, skin graft donor sites, burn wounds, etc. In the case of burn wounds, the wound dressings can be directly applied on a second or third degree burn. However, in case of extensive third degree burns, it is preferable to first graft the burn with meshed autologous skin. Application of the medicated GDP wound dressing directly on top of this autologous meshed graft will stimulate the closure of the meshed graft interstices, resulting in faster wound closure and concomitant reduction of infection risks and shortening of treatment time.

To facilitate application on the treatment site, the medicated GDP wound dressings can be manufactured in different forms. For instance, sheet- or film-like dressings can conveniently be applied onto burn wounds, shallow ulcers, skin graft donor sites and other types of shallow wounds. To reduce fluid evaporation and dehydration of the dressing and the underlying wound, the dressing can be covered with a flexible membrane, the water permeability of which is chosen so as to obtain an optimal moisture level of the wound. It is also possible to manufacture multi-layered GDP laminates. Each layer of such a laminate can have different release properties and contain a different active substance. Upon application on the wound this will result in the controlled release of the incorporated factors from the subsequent layers, according to a predefined sequential and temporal programme. This programme will depend in part on the release properties and biodegradation of the different layers, their thickness and on the properties of the incorporated factors. Obtaining such a controlled delivery of multiple drugs is considered desirable because it is known that the wound repair process occurs in different stages, each of which requires the involvement of different factors. For instance, one stage of wound healing consists of the development of granulation tissue. This phase may be stimulated for instance by administration of PDGF or FGF. In a next phase, the wound is closed by an epithelialization process, which may be stimulated by EGF. Inclusion of factors such as VEGF or PD-ECGF may optimize a process such as vascularisation which is often unsatisfactory and can be the underlying cause in chronic wounds such as ischaemic wounds. Which factor has to be released at which time point to obtain optimal healing results, depends partly on the type of wound. It is also known that sometimes the wound healing process can be aberrant leading to the formation of persistently heavy scars or keloids. Such keloid formation is predisposed by two main factors. The first is the location of the scar and the second is the genetic background of the patient. It is therefore anticipated that keloid formation results from the atopic or superfluous presence of certain factors and that the presence of certain layers within the wound dressing can be used to sequester these unwanted factors. Other factors that can be sequestered comprise those that can lead to superfluous production of to many collagen and/or elastin, thereby preventing phenomena such as skin contractions or keloid formation. It is also one of the advantages of the present invention that programmed delivery of several drugs is possible using only one dressing, i.e. without having to change wound dressings.

In case of deeper wound cavities, such as some types of pressure sores or chronic ulcers, it may be more convenient to fabricate the medicated GDP wound dressing in the form of microparticles, foams, pastes or other forms which are easily conformable to the wound shape. Microparticles may be fabricated according to any of the procedures known in the art, provided the activity of the incorporated active substances is not destroyed. To increase the shelf life of the medicated particles, it is also possible to lyophilize them. The resulting powder or granulate can be applied onto the wound either directly, in which case it will have the added benefit of adsorbing excess wound fluid, or it can be first rehydrated by incubation in a suitable aqueous solution. The medicated particles can also be formulated in a suitable excipient such as vaseline, paraffin oil, etc. so as to obtain a paste which can for instance be used to fill a cavity.

In one of the embodiments of the present invention, the pharmacologically active substance is incorporated into an affinity GDP matrix such as described above. In this case, the matrix contains, apart from gelatin, dextranox and an aqueous medium, also additional cross-linked, non-diffusible or otherwise immobilized compounds which have an affinity for the active substance. This results in a reduction of the release rate of the active agent and in some cases they may also stabilize the agent. Following are but a few examples of such affinity ligands which may be incorporated into GDP matrices.

One class is constituted by those molecules which display an affinity for heparin binding proteins, such as heparin or functional analogs of heparin such as heparan sulfate, chondroitin sulfate, dermatan sulfate, dextran sulfate or any other non-toxic polyanionic group displaying sufficient affinity for an incorporated heparin-binding factor. Examples of such factors include FGFs, HB-EGF, amphiregulin and betacellulin.

Another example of affinity ligands may consist of hydrophobic chains, which could retard the release of incorporated active agents with a hydrophobic nature. Incorporation of such chains in GDP could be achieved for instance by the use of partially hydrophobized dextranox derivates as cross linkers. These can be obtained for instance by partial esterification of dextran with fatty acids (e.g. caproic acid, stearic acid) followed by periodate oxidation of the thus obtained dextran esters.

It will be clear to the person skilled in the art that the fabrication of medicated wound dressings with controlled release properties is but one application of the present invention. Many other possible applications of the use of GDP as a controlled release matrix can be envisaged. The following possibilities are intended only as examples and do not in any way limit the range of possible applications.

GDP can for instance be used for the fabrication of devices for transdermal drug delivery. A GDP patch containing a transdermally deliverable drug can be attached to the skin, enabling a slow release of the drug over a prolonged time period. In another application, GDP microparticles loaded with a particular drug can be injected intravenously, subcutaneously or intramuscularly. Equipped with a tagging system, such injected microparticles may be used for topical administration of compounds with which the microparticles were loaded. In principle, all drugs for which a slow release over a period ranging between a few days to a few weeks is desirable are eligible for incorporation in GDP microparticles. Examples include, but are not limited to, anticancer drugs, hormones, vaccines, contraceptives, cardiovascular drugs, neuroactive drugs etc.

FIGURE LEGENDS

FIG. 1: Fluid loss of GDP films covered with either an Exkin or a Pebax 1205 film.

Figure 2:
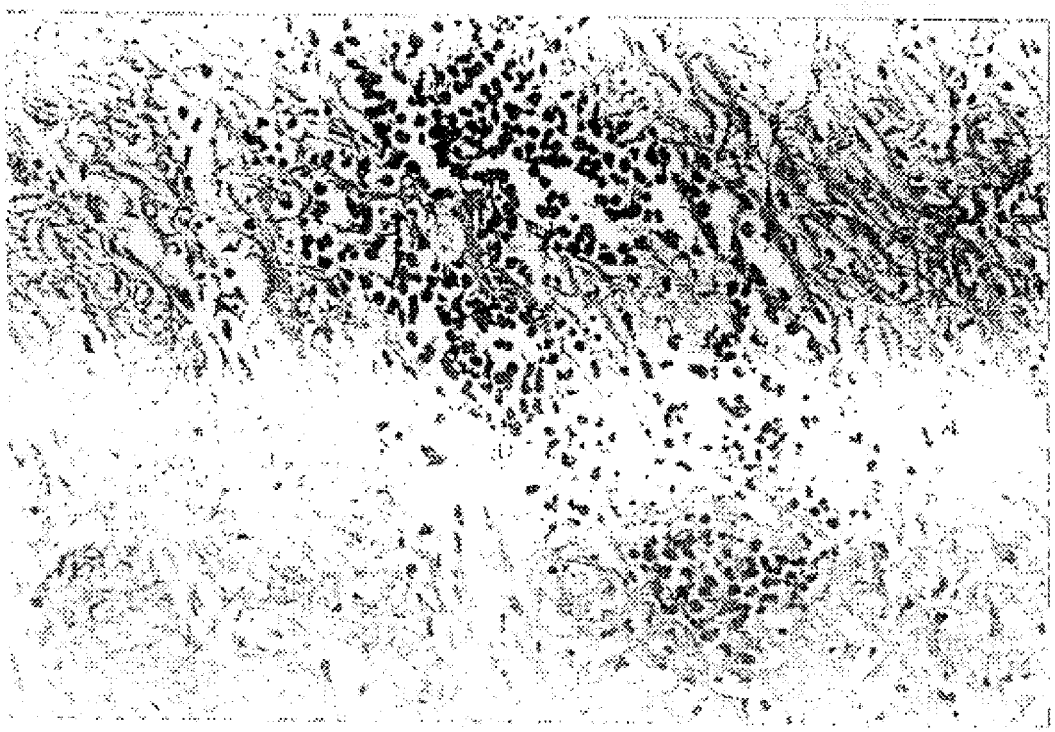

FIG. 2: Histological section of full thickness pig wound, 20 days after application of GDP film, showing limited presence of inflammatory foci.

Figure 3:

FIG. 3: Histological section of full thickness pig wound, 20 days after application of Duoderm, showing presence of many granulomas.

Figure 4:
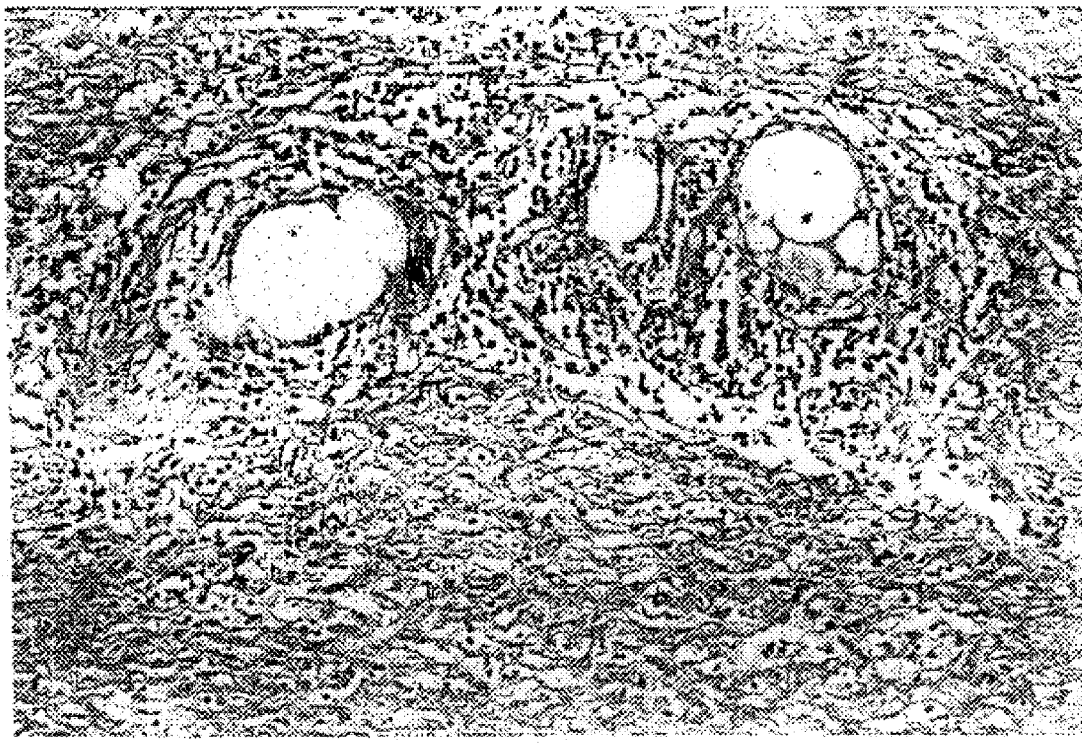

FIG. 4: Histological section of full thickness pig wound, 20 days after application of Duoderm, showing presence of vacuoles containing remnant Duoderm particles FIG. 5: Release of AR1 oligopeptide, as measured in an elution system. AR1 peptide was incorporated during the production of the film.

Figure 6:
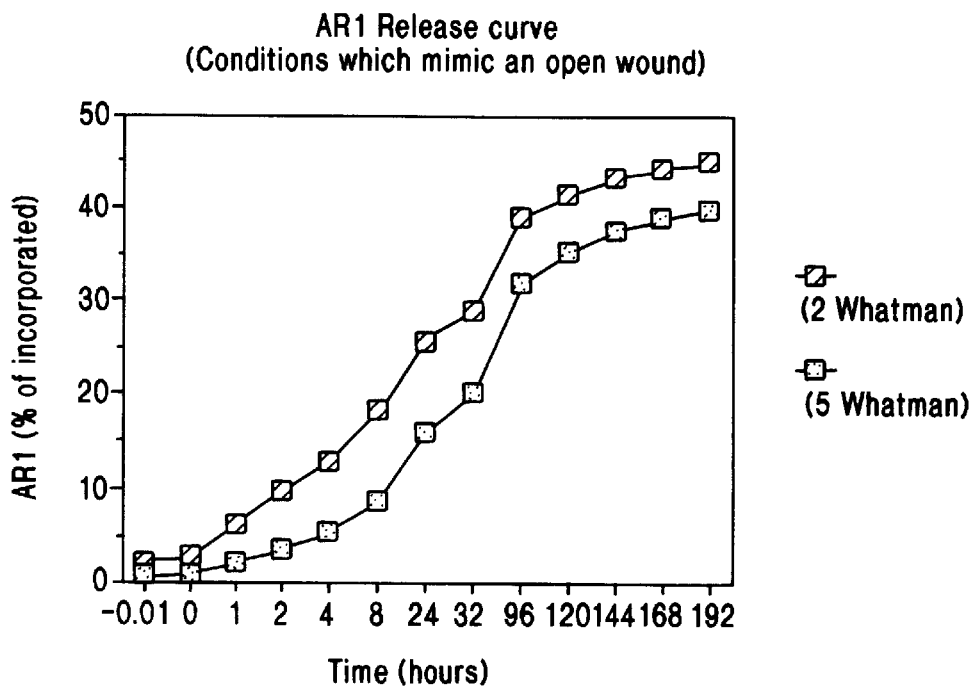

FIG. 6: Release of AR1 peptide, as measured in a paper wick system, mimicking the wound situation.

Figure 7:
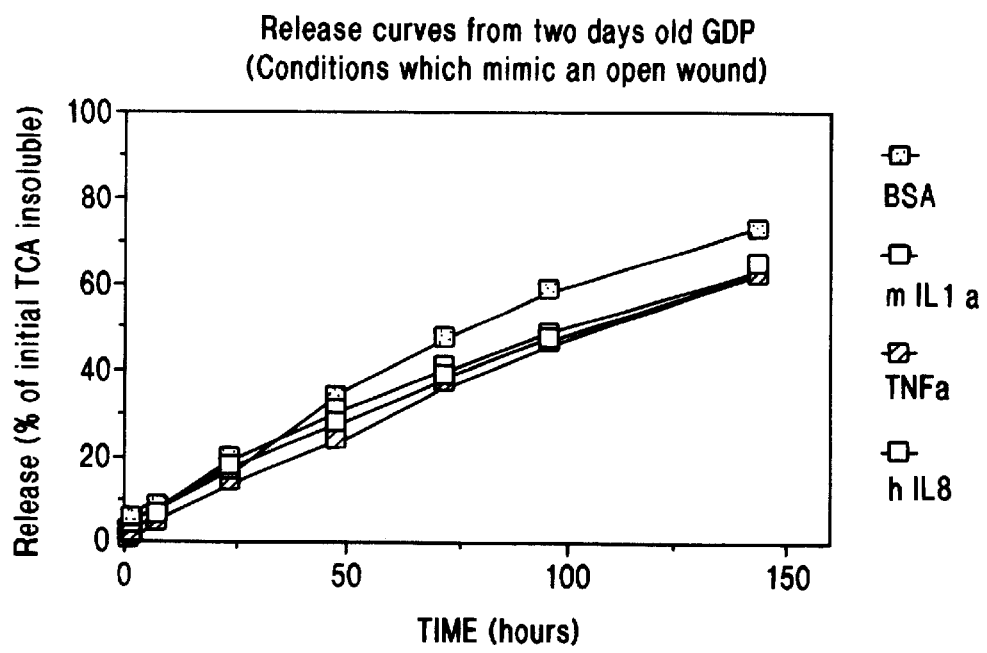

FIG. 7: Release of iodinated test factors BSA, mIL1α, TNFα, and hIL-8 from a 2 day-old GDP film, measured in a paper wick release system.

Figure 8:
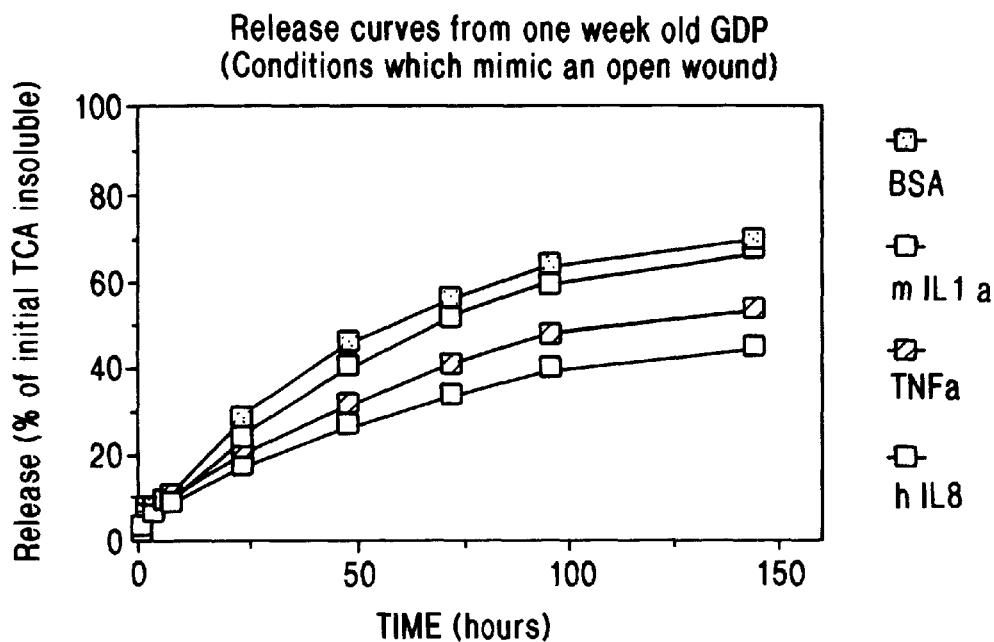

FIG. 8: Release of iodinated test factors BSA, mIL1α, TNFα, and hIL-8 from a 1 week-old GDP film, measured in a paper wick release system.

Figure 9:
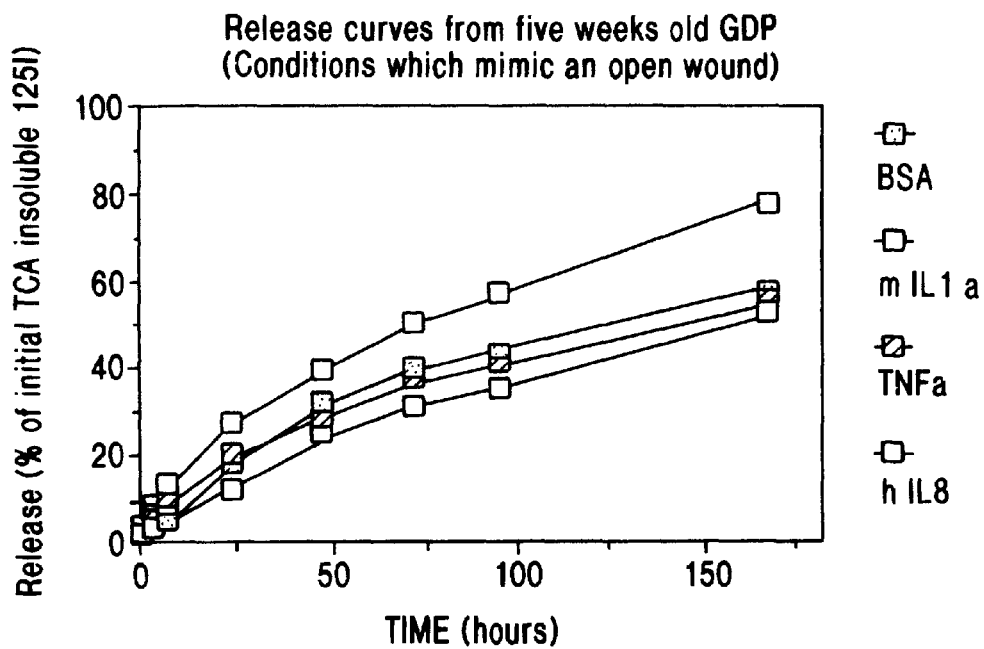

FIG. 9: Release of iodinated test factors BSA, mIL1α, TNFα, and hIL-8 from a 5 weeks-old GDP film, measured in a paper wick release system.

Figure 10:
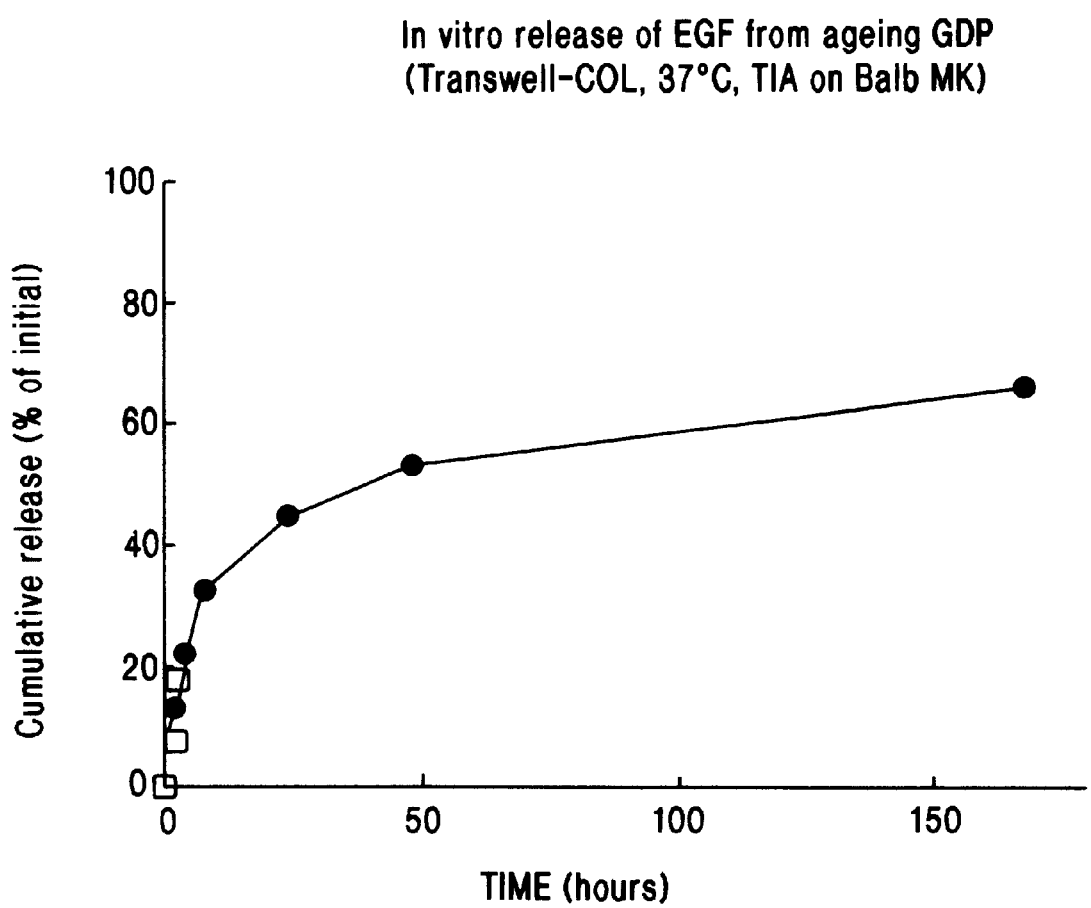

FIG. 10: Release of active EGF from a GDP film, measured in a paper wick release system.

FIG. 11: Release of polyanions from hydrogel affinity matrix samples

A) Five days after the hydrogel production

B) Two months after the hydrogel production

FIG. 12: Temperature dependence of the hydrogel storage modulus in function of hydrogel storage time and hydrogel dextran sulphate content.

FIG. 13: Water uptake by dextran sulphate-containing gelatin hydrogels at 20° C. and 37° C.

Figure 14:
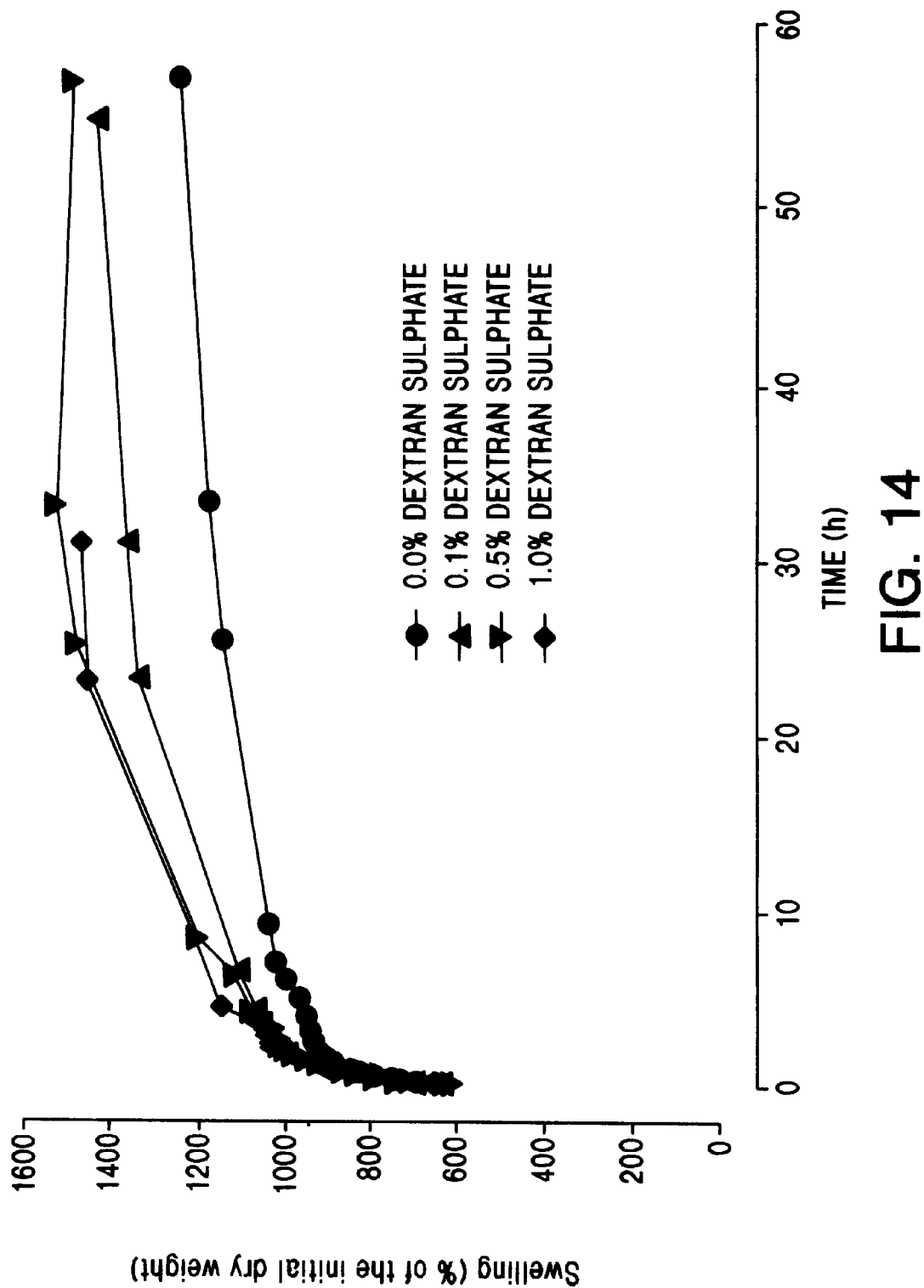

FIG. 14: Water uptake at 37° C. by gelatin hydrogels containing different concentrations of dextran sulphate FIG. 15: Wound healing in pig A) Reduction of the initial wound area by wound contraction and re-epithelalization B) Reduction of the initial wound area by wound contraction FIG. 16: Wound healing in pig A) Reduction of the initial wound perimeter by wound contraction B) Reduction of the initial wound perimeter by wound contraction and re-epithelialization FIG. 17: Rate of wound healing Radial progression towards wound closure: length of daily advance of the wound margins and the re-epithelialization towards wound center

EXAMPLES

Example 1

Production of GDP Film

Oxidation of Polysaccharide

Twenty g of pyrogen-free clinical grade dextran with molecular mass 60,000–90,000, such as commercialised by ICN (ref:101513) are dissolved in 200 ml of phosphate buffer (pH6). A solution which is prepared from 7.92 g of periodate and 20 ml water is subsequently added, with agitation, to the dextran solution. After two hours at room temperature, the oxidized polysaccharide is isolated from the reaction medium by precipitation with a third solvent.

Before precipitation, iodate formed during the reaction can be eliminated by treating the reaction solution with 30 g of potassium iodide dissolved in 150 ml of diluted hydrochloric acid (0.05M), before pouring the mixture into 500 ml of methanol to precipitate the oxidized dextran.

Alternatively, the reaction mixture can be dialysed against pure water and, when all the periodate is eliminated, the solution can be concentrated to isolate the polysaccharides. Concentration can be performed for instance by lyophilisation. It has been established by titrimetric analysis using hydroxylamine that 20% of the secondary alcohol groups of the dextran were oxidized.

Preparation of a GDP Film

Two g of gelatin (Isoelectric point 7.01, gel strength 203 on the Bloom scale) is dissolved at 40° C. in 10 ml of phosphate buffer (pH 8, ionic strength 0.2). Ten g of dextranox prepared as describe above is dissolved in 10 ml of phosphate buffer (pH 8, ionic strength 0.2) and warmed to 40° C. Both solutions (at 40° C.) are mixed and subsequently poured into a cast made of two glass plates separated by spacers of 1 mm thickness. The cast is then placed overnight at 4° C. during which gelation and cross-linking take place. After removal of the glass plates a flexible 1 mm thick film is obtained which is water-insoluble.

Example 2

Preparation of a GDP Film Laminated to a Plastic Foil

Preparation of a GDP Film Laminated to a Plastic Foil

Two 9 of gelatin (Isoelectric point 7.01, gel strength 203 on the Bloom scale) is dissolved at 40° C. in 10 ml of phosphate buffer (pH 8, ionic strength 0.2). Ten g of dextranox prepared as describe above is dissolved in 10 ml of phosphate buffer (pH 8, ionic strength 0.2) and warmed to 40° C. Both solutions (at 40° C.) are mixed and subsequently poured into the reservoir of a film casting device (Braive Instruments). The casting plate of the film casting device has been fitted beforehand with a 20 $\mu$m thick plastic film of the type Pebax X 1205 (available from Elf Atochem, France). The sliding knife and reservoir of the casting device is set at the desired film thickness. The casting plate of the device is thermostatized at 15° C. to shorten the gelling time of the casted polymer mixture and thus ensure even film thickness. Film casting is performed by moving the sliding knife and reservoir with a preset speed (for instance 2 mm/sec.) over the casting plate, thus leaving a thin polymer film onto the plastic foil. After casting the GDP film onto the Pebax foil, it is allowed to gel and cross link overnight at 4° C. The result is a GDP film firmly laminated onto the 20 $\mu$m thick Pebax foil. Alternatively, depending on the desired water vapour permeability, another type of plastic foil can be used, for instance Exkin (produced by Utermöhlen NV, The Netherlands). This plastic foil, which can be used as a semi-occlusive wound dressing, has a bilayer structure consisting of a macroporous and a microporous layer. Due to its higher porosity, it has a much higher water vapour permeability as compared with the Pebax X 1205 foil.

Comparison of the Water Loss Due to Evaporation of GDP Films Laminated to Different Plastic Foils.

A 1 mm thick GDP film is laminated to either a 20 $\mu$m thick Pebax X 1205 foil or to an Exkin foil and placed with the GDP side down onto a metal plate heated to 37° C. The upper side of the laminate (i.e. the plastic foil) is exposed to the air at ambient temperature (approximately 20° C.). At regular time points, water loss of the films is measured by determining the residual weight of the laminates. This residual weight is expressed as percentage of the original weight and is displayed in FIG. 1. From the results, it is clear that the Pebax X 1205 foil has a better barrier function and may thus be suited for the preparation of GDP laminate wound dressings intended for the treatment of wounds producing low amounts of exudate. On the contrary, the Exkin membrane allows a higher evaporation rate and is consequently more suited for preparation of GDP laminate wound dressings intended for the treatment of wounds producing high exudate volumes.

Example 3

In Vitro Cytotoxicity Testing

One of the most important prerequisites for the clinical usefulness of a wound dressing is that it has a high biocompatibility. Therefore, it is essential that the material displays a very low or even non-existent cytotoxicity. Cytotoxicity of a biomaterial can be measured in vitro by incubating the material for a prolonged period together with suitable target cells. If the material is cytotoxic, the target cells will be killed and the number of surviving cells will be inversely related to the cytotoxicity. This can conveniently be done in a so-called methylcellulose toxicity test, as described by Van Luyn (Doctoral thesis, University of Groningen, The Netherlands, 1992; ISBN-90-9005113-9). As target cells, different cell types relevant for wound healing can be used, such as fibroblasts, keratinocytes and endothelial cells.

Cytotoxicity of GDP Film for Murine 3T3 Fibroblasts

Twenty five thousand Swiss 3T3 fibroblasts are seeded per well in 12-well tissue culture plates. The cells are seeded in standard growth medium containing 1.125% methylcellulose. The cells are allowed to attach for 24 hours at 37° C. Subsequently, a 113 mm$^2$ circular piece is punched from a GDP film and placed on top of the methylcellulose gel covering the seeded cells. For comparison a similarly sized piece of the hydrocolloid ulcer dressing Duoderm (obtained from Convatec, UK) is placed on another well. A third well serves as negative control and receives no test material. All tests are carried out in triplicate. After 6 days at 37° C., the amount of surviving cells is determined by MTT staining, a method which specifically detects metabolically active cells. The percentage of surviving cells (relative to the negative control) is 22% and 42% with Duoderm and GDP, respectively. This indicates that GDP has a considerably lower cytotoxicity towards these fibroblasts than the commonly used ulcer dressing Duoderm.

Cytotoxicity of GDP Film for Human Skin Fibroblasts

Twenty five thousand primary fibroblasts isolated from human skin are seeded per well in methylcellulose-containing medium in 12-well tissue culture plates as described above. After 24 hours at 37° C., circular pieces of Duoderm or GDP are applied on top of the methylcellulose gel. The GDP films used in this experiment have been sterilized by gamma irradiation. Two irradiation doses are used: one film receives 2.5 MRad, another film receives 0.6 MRad. The pieces are left in place for 6 days, after which the percentage of surviving cells relative to a negative control is determined using MTT staining. The percentage of surviving cells is 63, 59 and 44% relative to the negative control for GDP irradiated with 2.5 MRad, GDP irradiated with 0.6 MRad and Duoderm, respectively. Again, these figures demonstrate that GDP film is considerably less cytotoxic for fibroblasts than Duoderm. Moreover, irradiation does not induce cytotoxicity in the GDP films.

Cytotoxicity of GDP Film for Murine Balb/MK Keratinocytes

Twenty five thousand murine Balb/MK keratinocytes are seeded per well in methylcellulose-containing medium in 12-well tissue culture plates as described above. After 24 hours GDP film and Duoderm are applied onto the methylcellulose gel and left in place for eiher 3 or 6 days. After 3 days, the percentage of surviving cells is 65 and 30% with GDP and Duoderm, respectively. After 6 days of incubation with the wound dressings, the percentage of surviving cells is 32 and 9% with GDP and Duoderm, respectively. This again confirms the superior cytotoxicity properties of GDP above Duoderm.

Cytotoxicity of GDP Film for Human Skin Keratinocytes

Twenty five thousand primary human keratinocytes isolated from a skin biopsy are seeded per well in hydroxyethylcellulose-containing medium in 12-well tissue culture plates as described above. In this case, hydroxyethylcellulose (marketed under the trade name Idroramnosan by Vevy, Italy) is used instead of methylcellulose because we have found the former material to be more suitable to support the attachment and proliferation of the human keratinocytes. After 24 hours at 37° C., pieces of GDP film and Duoderm are placed onto the gel and left in place for 3 or 6 days. After three days, the percentage of surviving cells is 79% and 13% with GDP and Duoderm, respectively. After 6 days, 35 and 1.4% of the cells survive with GDP and Duoderm, respectively. Once more, this underscores the superior properties of the GDP dressing, since it has only a limited cytotoxicity for keratinocytes, while incubation with Duoderm results in almost 100% cell death within 6 days.

Conclusions on the In Vitro Cytotoxicity Testing

The in vitro cytotoxicity tests described above show that GDP has a very favourable and low cytotoxicity level. We have compared GDP with Duoderm because both dressings are of a similar type and because the latter is a very frequently used dressing for the treatment of chronic ulcers. The fact that GDP is superior to Duoderm with respect to cytotoxicity underscores its clinical applicability as a wound dressing.

Example 4

In Vivo Biocompatibility Testing: Implantation in Mice

GDP film of 1 mm thickness is prepared as described in example 1. GDP strips of 2×30 mm are implanted subcutaneously on the back of Balb/C mice. Per mouse, two strips were implanted bilaterally, parallel with the spine, under the panniculus carnosus. At 1, 2, 4, 8 and 16 days after implantation, the implantation sites are controlled macroscopically and then completely excised. Per time point, two mice are used; Excised sites are processed for histology and evaluated microscopically. As controls, similarly sized strips of Duoderm are implanted in a separate set of mice, and in yet another set of mice subcutaneous pockets are made which receive no implant.

Macroscopically, slight redness is observed with Duoderm. New tissue is found to invade the material. Duoderm, however, stays largely intact. With GDP, no macroscopically visible reactions are observed and the material stays intact.

Histologically, Duoderm shows slight inflammation on day 1, with increasing infiltration of neutrophils from day 2 onwards. At days 4 or 16, strong inflammation is observed with infiltration of neutrophils and macrophages. Lipid droplet-containing macrophages are present and the inflammation is more of the chronic type, with some signs of foreign body reaction.

With GDP, a strong neutropbil infiltration is also observed initially. However on day 16, the inflammatory response largely disappears. No signs of foreign body reaction are observed. On days 8 and 16, slightly increased fibroblast proliferation is observed around the implant. The GDP implant remains almost completely intact, apart from some slight erosion at the edges.

These results confirm the biocompatibility of GDP. The quite normal inflammatory response initially observed resolves rapidly, and no signs of long term inflammatory events or foreign body reactions are observed. This means the material is well suited for the fabrication of wound dressings.

Example 5

In Vivo Testing: Full Thickness Wounds in Pigs

Twenty-four full thickness square wounds of 2×2 cm are made on the back and sides of a 75 kg castrated male Belgian Landrace pig. The wounds are made under general anaesthesia (Stresnil, Halothane and Diprivan), by excising the skin to the fascia, taking care to include no muscle with the excised tissue. Each side of the animal receives two rows of 6 wounds, parallel to the backbone. After surgery, 8 wounds are covered with a 5×5 cm sheet of GDP film of 1 mm thick, prepared as described in example 1. Eight other wounds are treated with a 5×5 cm sheet of Duoderm, while the remaining eight wounds serve as controls. All wounds are subsequently covered with Tegaderm (an occlusive polyurethane dressing) and fixed with Fixomull and Velpo bandages. At 2, 5, 9 and 20 days after surgery, two wounds of each treatment are examined macroscopically and subsequently fully excised for histological analysis. Epithelisation and contraction of the wounds are quantitatively evaluated by planimetry. Macroscopically, both GDP and Duoderm appear to stimulate granulation tissue formation on days 5 and 9 after surgery, with the wound bed protruding several mm above the surrounding skin. Both GDP and Duoderm result in increased epithelisation on day 9. At day 20 after surgery, all wounds are closed and no gross macroscopical difference between the three treatments is observed. For histological analysis, wound biopsies are fixed in 10% paraformaidehyde, sectioned at 5 $\mu$m and stained either with haematoxylin/eosin or with Masson's Trichrome. The progression of the epithelial margin is measured on both sides of each wound, using two representative tissue sections. The results are expressed in Table 1 and indicate a slightly increased epithelisation with GDP on day 5, while on day 9, the difference between the three treatments was non-significant. On day 2 after surgery, the general appearance of all wounds is similar, although Duoderm-treated wounds contain more red and inflammatory cells and several inflammatory foci of polymorphonuclear neutrophils and macrophages/monocytes. At that time point, GDP is still largely intact. At five days after surgery, those parts of GDP which are in contact with the tissue are strongly invaded by white cells while the parts in contact

TABLE 1

Epithelialisation rates of full thickness pig wounds treated with GDP, Duoderm or Tegaderm, measured directly on histological sections (a) or on micrographs of histological sections (b). Significance of the results is displayed in the second table.

| Treatments | | Days after wounding | | |
|---|---|---|---|---|
| | | 2 | 5 | 9 |
| GDP | a | 212.3 ± 227.3 | 1898.0 ± 736.9 | 2087.2 ± 203.7 |
| | b | 197.3 ± 160.7 | 1779.4 ± 271.4 | 1974.4 ± 332.48 |
| Duoderm | a | 415.0 ± 297.8 | 1651.0 ± 523.5 | 2578.5 ± 473.8 |
| | b | 360.6 ± 166.7 | 1415.7 ± 445.8 | 2504.8 ± 240.7 |
| Tegaderm | a | 651.6 ± 278.2 | 1091.5 ± 276.3 | 2215.2 ± 384.4 |
| | b | 613.9 ± 427.2 | 844.9 ± 403.5 | 2202.6 ± 370.9 |

Analysis of the variance

ANOVA (F-test, Bonferroni method), NS: not significant, S : significant at 95%, SS significant at 99%.

| | | Days after wounding | | |
|---|---|---|---|---|
| | | 2 | 5 | 9 |
| GDP versus Duoderm | a | NS | NS | S |
| | b | NS | NS | SS |
| GDP versus Tegaderm | a | S | S | NS |
| | b | S | SS | NS |
| Duoderm versus Tegaderm | a | NS | NS | NS |
| | b | NS | NS | NS | with crust or fibrin clot are nearly intact. In Duoderm-treated wounds, a dense inflammatory reaction is seen, including the formation of granulomas. At day 9 after surgery, GDP-treated wounds are filled with granulation tissue above the level of the surrounding skin. The GDP material in contact with tissue is totally invaded by white cells, while the crust-contacting GDP is mostly intact. Some granulomas are present, but much less than with Duoderm. The deeper dermal tissue contains few inflammatory cells and consists of dense scar tissue with regularly arranged fibroblasts embedded in dense collagen. In Duoderm-treated wounds, a similar scar tissue is present, but the granulomas are by far more abundant than with GDP (FIGS. 2 and 3). Tegaderm-treated wounds contain almost no granulomas. At 20 days post-surgery, all wounds are epithelialized. Granulomas are very abundant in Duoderm-treated wounds, much less abundant in GDP-treated wounds and only occasionally seen in Tegaderm-treated wounds. Scar tissue of Duoderm-treated wounds shows many vacuoles containing remnant Duoderm particles (FIG. 4). This indicates a strong, moderate and weak inflammatory foreign body response with Duoderm, GDP and Tegaderm, respectively. The conclusion of this test is that GDP is a highly biocompatible material, which generates a significantly lower long term inflammatory response than the widely used ulcer dressing Duoderm. Moreover, the material is completely biodegradable over a period of 1–3 weeks, although it remains largely intact for about 5 days following application.

Example 6

Controlled Release of an Oligopeptide from GDP Films

Preparation of a Polypeptide-loaded GDP Film

Two g of gelatin (Isoelectric point 7.01, gel strength 203 on the Bloom scale) is dissolved at 40° C. in 10 ml of phosphate buffer (pH 8, ionic strength 0.2). One g of dextranox prepared as described by Schacht et al. (Pat. appl. 0308330) is dissolved in 10 ml of phosphate buffer (pH 8, ionic strength 0.2) and warmed to 40° C. To both solutions, 0.1% thimerosal is added as a preservative. To 10 ml of the gelatin solution, 100 µg of a biotinylated 21-mer oligopeptide (AR1) corresponding to the N-terminal part of the growth factor amphiregulin is added. The AR1 oligopeptide has the following amino acid sequence: Biotin-GG-VKPPQDKTESENTSDKPKR-CONH$_2$. Biotinylation of this oligopeptide was carried out only to facilitate its subsequent quantization but is otherwise not relevant for the result of the release experiments. Against this peptide a polyclonal antiserum raised in rabbits is available (antiserum RB 425), which allows detection of the peptide in an ELISA test system with a sensitivity of 2 ng/ml. Both the dextranox and peptide-containing gelatin solutions (at 40° C.) are mixed and subsequently poured into a cast made of two glass plates separated by spacers of 1 mm thickness. The cast is then placed overnight at 4° C. during which gelation and cross-linking take place. After removal of the glass plates a flexible 1 mm thick film is obtained which is water-insoluble. From this film, circular discs with a surface area of 400 mm$^2$ were punched for performing the release studies.

In Vitro Release Studies

Release Testing Using an Elution System

Figure 5:
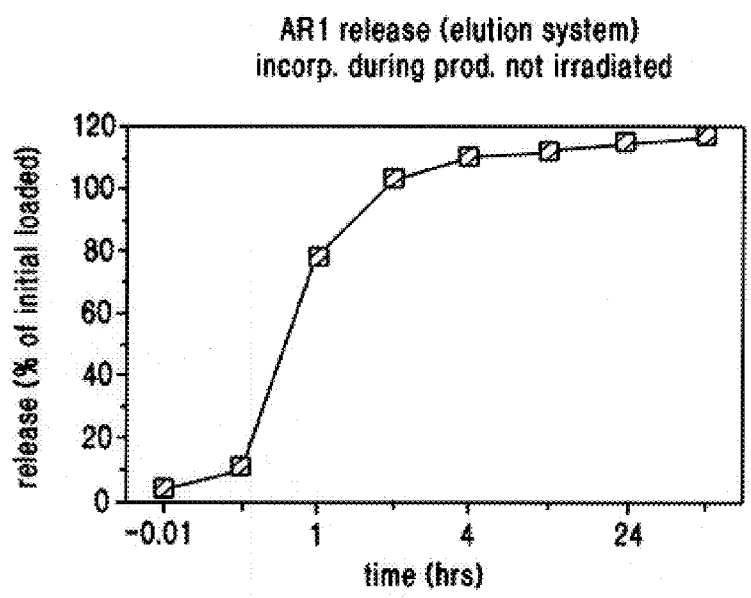

Circular AR1 peptide-containing GDP discs with a volume of 400 µl are briefly rinsed in Phosphate Buffered Saline (PBS) and incubated with slight agitation (approx. 60 rpm on an orbital shaker platform) in 4 ml of PBS containing 0.1% casein. The release test is carried out at an ambient temperature of 22° C. After 0, 1, 2, 4, 8, 24, 48 and 96 hours of incubation, 300 µl of the incubation solution is removed, snap-frozen in liquid nitrogen and stored at −20° C. After each sample removal, 300 µl of fresh PBS-casein buffer is added to the incubation vessel to maintain a constant extraction volume. After completion of the elutions, the samples are thawed, diluted 1/1, 1/10 an 1/100 and the amount of AR1 peptide is quantitated in an AR1-ELISA using the AR1-specific RB425 antibody as the first antibody and an alkaline phosphatase-conjugated anti-rabbit second antibody. The obtained results are shown in FIG. 5. The amount of AR1 released is expressed as percentage of the original amount of AR1 which is incorporated in the GDP disc. It can be seen that all the incorporated peptide is released within approximately 4 hours. This demonstrates that, despite the presence of 4 lysines in the peptide, no appreciable irreversible cross-linking of the peptide to the matrix has taken place.

Release Testing Using a Wound-mimicking System

For evaluation of release kinetics of controlled delivery wound dressings, an elution test system as described above is not ideal. Since the elution is carried out by means of an active extraction procedure, the release in such a system is much faster than would be observed in a wound. Therefore, we have adopted an alternative test system which mimics the wound situation with greater accuracy. This system has also been described by Shinde and Erhan (Bio-Med. Mat. Eng. 2: pp. 127–131, 1992) for determining the release properties of insulin-loaded flexibilized gelatin films. In this system, circular GDP discs (400 µl) are placed on a wick which is on its turn placed in a petri dish containing 4 ml of extraction fluid (PBS containing 0.1% casein). The wick is constructed of either 2 or 5 stacked Whatman 3MM filter paper discs with the same diameter as the GDP test slice. In case of a wick with 2 Whatman discs, the top surface of the wick is level with the surrounding extraction fluid. In case of a wick with 5 Whitman discs, the top surface of the wick is slightly higher than the level of the extraction fluid. The release test is carried out at 22° C. After placing the AR1-containing GDP test slice on the wick, the petri dish is closed and 300 µl samples are removed from the extraction fluid at regular time points as described above. AR1 present in the samples is quantitated in an AR1-specific ELISA system as described above. The results are shown in FIG. 6. In this example, between 45% and 50% of the incorporated AR1 peptide is released, over a time period of approximately 5 days. The fact that no 100% release is obtained is partly due to retention of some AR1 in the wick. Nevertheless, the release of AR1 in this system can be considered as highly efficient, and with a kinetics profile which is suitable for application in a wound dressing.

Example 7

Controlled Release of Iodinated Test Polypeptides (IL-1α, IL-8, EGF, BSA) from GDP Films Preparation of the Films For application in the manufacturing of growth factor-containing medicated wound dressings, GDP should also allow the efficient release of larger peptide factors. To evaluate this, a number of test proteins with different properties is used. To facilitate the release studies, these proteins are iodinated prior to their incorporation. The test proteins used are listed below:

TABLE 2

| protein | MW (kDa) | GRAVY | pI | % lysine |
|---------|----------|-------|------|----------|
| BSA     | 69       | -4.3  | 5.69 | 10.7     |
| IL-1α   | 17       | -1.65 | 5.09 | 9.2      |
| TNF-α   | 17       | -2.09 | 7.26 | 12.8     |
| IL-8    | 8        | -4.88 | 9.59 | 12       |

Iodization is performed according to the iodobeads method (Pierce, US). The specific activity obtained ranges between 3000 and 8000 cpm/ng of protein.

GDP films containing the iodinated factors are prepared using similar procedures as described above for AR1-containing films, except that the gelatin solution is presterilized by autoclaving. The concentration of iodinated test proteins in the GDP matrix is approximately 8 µg/ml.

Release Tests

The release tests are set up using the wick system as described above for AR1, using a wick containing 5 stacked Whitman 3MM filter discs. To simulate the wound conditions more closely, the release test is carried out in a thermostatized incubator at 37° C. At predefined time points, 100 µl extraction fluid is removed and 100 µl fresh fluid is added to maintain a constant extraction volume. To quantitate the amount of labelled protein released, the radioactivity present in the removed extraction liquid samples is measured in a gamma-counter. To additionally evaluate the stability upon storage of the protein-loaded GDP films, release profiles are determined in films stored at 4° C. for 2 days, 1 week and 5 weeks. Previous experiments have shown that, after a storage time of the labelled proteins of 52 days at -20° C., up to 25% of the incorporated iodine could be released from the proteins due to radiolysis. Therefore, extraction liquid samples are first precipitated with TCA prior to the radioactivity measurements, to be sure that only protein-associated radioactivity is quantified. At the end of the experiment, residual radioactivity is also determined in the GDP discs and in the filter paper wick.

The results are shown in FIGS. 7–9. Approximately 50–80% of the incorporated proteins are released in a period of 6 days. The amount of residual protein in the GDP disc and the wick ranged from about 10 to about 22%. The results confirm that also for larger proteins, release occurs with high efficiency and according to kinetics which are favourable for application in medicated wound dressings. Also, the stability of the matrix proves to be sufficient to allow prolonged storage.

Example 8

Controlled Release of Bioactive EGF From GDP Films

The potential of GDP films to release oligopeptides and proteins is well established, as demonstrated in examples 1 and 2. For effective use, it is however also important that the biological activity of the released factors is preserved. To demonstrate that this is indeed the case, a GDP film is produced containing the growth factor EGF. EGF stimulates a wide variety of cell types, including keratinocytes and fibroblasts, and is generally accepted as a suitable candidate factor for stimulating the wound repair process. Several companies are actively involved in developing EGF for therapeutical purposes. Therefore, EGF can be regarded as an appropriate molecule to be incorporated in medicated wound dressings such as those disclosed in the present invention.

Preparation of GDP Film Containing EGF

Mouse submaxillary gland EGF is obtained from Sigma (US).

GDP film containing EGF is prepared according to the procedure described above for AR1. The gelatin used for the preparation of the films has been sterilized by a 0.6 MRad gamma radiation dose before dissolution. The final concentration of EGF in the film is approximately 10 µg/ml. The EGF-containing GDP film is stored at 4° C. for 1 week until use in the release test.

Release Experiment

To simulate release under wound-like conditions, a new test system is set up. A disc of 113 mm² is punched from the GDP film and placed on the filter membrane of a Trans-well filter cup (Costar, US) with a filter pore size of 3 µm. The cup is subsequently placed in a well from a 6-well test plate. The well contains 1 ml of extraction fluid consisting of PBS containing 0.05% CHAPS and 0.1% casein. The Transwell cup is inserted in such a way that the membrane just touches the surface of the extraction fluid. After assembling the system, the 6-well plate is closed with a lid and incubated at 37° C. in a thermostatized incubator. At selected time points, 50-µl samples are removed from the extraction fluid and frozen at -70° C. After each sampling, fresh extraction fluid is added to the well in order to maintain a constant liquid volume. At the end of the test, all samples are thawed and the amount of EGF is quantitated using a bioassay. In this bioassay, EGF or test samples are added to a culture of growth-arrested Balb/MK keratinocytes. Upon stimulation with EGF these cells increase their proliferation rate. This proliferation rate can in turn be quantitated by measuring the amount of tritium-labelled thymidine incorporated in the DNA of the cells. After comparison of the tritium thymidine incorporation values of test samples with the values obtained using known concentrations of EGF, the amount of active EGF in these test samples can be accurately determined.

The results of the release test are shown in FIG. 10. More than 60% of the incorporated EGF is released over a period of about 7 days. This example effectively demonstrates that a wound repair-promoting growth factor can be incorporated in GDP and subsequently efficiently released in a bioactive form. GDP matrices according to this invention are therefore suitable controlled release devices for the fabrication of medicated wound dressings.

Example 9

SIPN Incorporation Technology and Release Experiments

SIPN Incorporation Technology

The GDP hydrogel films are prepared as demonstrated in example 1. Polyanions are incorporated into the hydrogel matrices during the production before gelatin hydrogel cross-linking to result in a SIPN (semi-interpenetrating polymer network). The hydrogel matrices films consist of 5% dextran dialdehyde (20% oxidized dextran, MW 70000), 10% gelatin type A and one of the following polyanions: chondroitin sulphate (MW 15000), dextran sulphate (MW 40000 or 400000–600000), at a final concentration of 0.5% (5 mg/ml) or heparin (at a final concentration of 200 $\mu$g/ml). To achieve a homogenous distribution of the incorporated polyanions in the hydrogels, the polyanions are first mixed in the dextran dialdehyde solutions before mixing the polyanion-containing dextran sulphate solutions with gelatin solutions. The polyanions used are:

Dextran sulphate (MW 400000–600000), ICN Biochemicals, Cleveland, Ohio, Lot N° 64914.
Dextran sulphate (MW 40000), ICN Biochemicals, Cleveland, Ohio, Lot N° 66617.
Chondroitin sulphate (MW 15000), RUG
Heparin sodium salt from Porcine intestinal mucosa sodium salt Grade I 175 USP/mg Sigma Chemical Company St Louis, Mo. Lot N 63H1017. (MW 6000–20000).
Heparin sodium salt from Porcine intestinal mucosa sodium salt Grade I 175 USP/mg Sigma Chemical Company St Louis, Mo. Lot N 21H7705. (MW 4000–6000).

The affinity matrix films are stored at 4° C. for either 5 days or two months in sealed plastic packages to prevent hydrogel drying.

Release Experiments

To quantify the release of polyanions from the affinity matrix, film samples (3.8 cm$^2$) are immersed in 3 ml PBS/thimerosal 0.02% and incubated at 37° C. for 7 days with agitation (1 rotation/sec). At particular time points, the extraction medium is removed, immediately stored at 4° C., and replaced by fresh extraction medium. At the end of each experiment, the amounts of polyanions released in the medium are quantified by a calorimetric method which uses dimethylmethylene blue (Farndale et al BBA 883: 173–177, 1986).

Figure 11A:
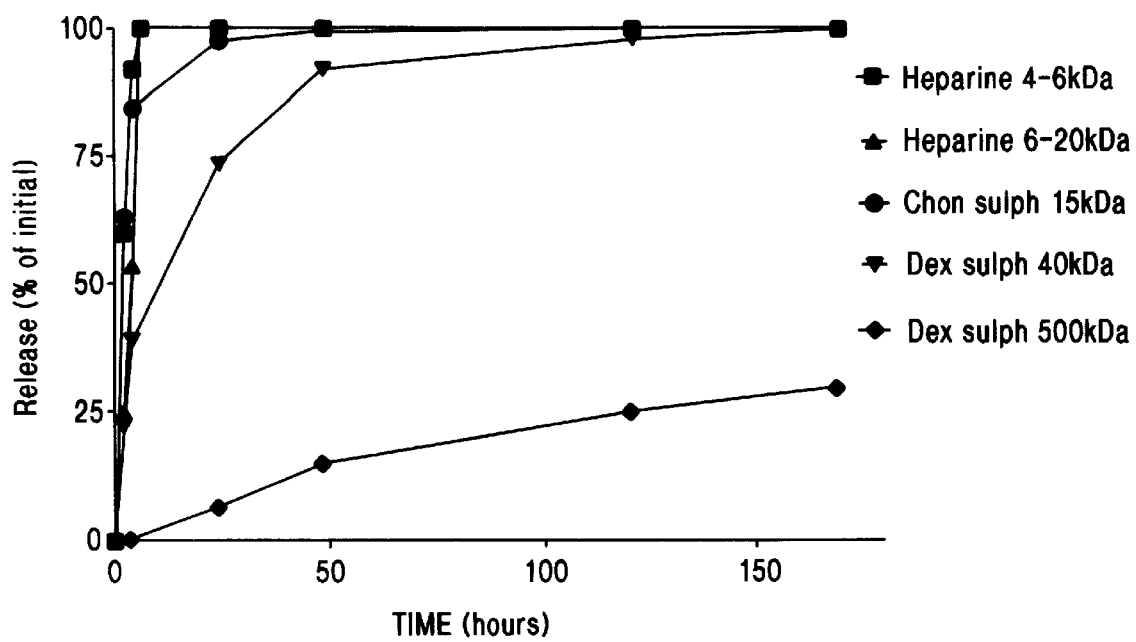
Figure 11B:
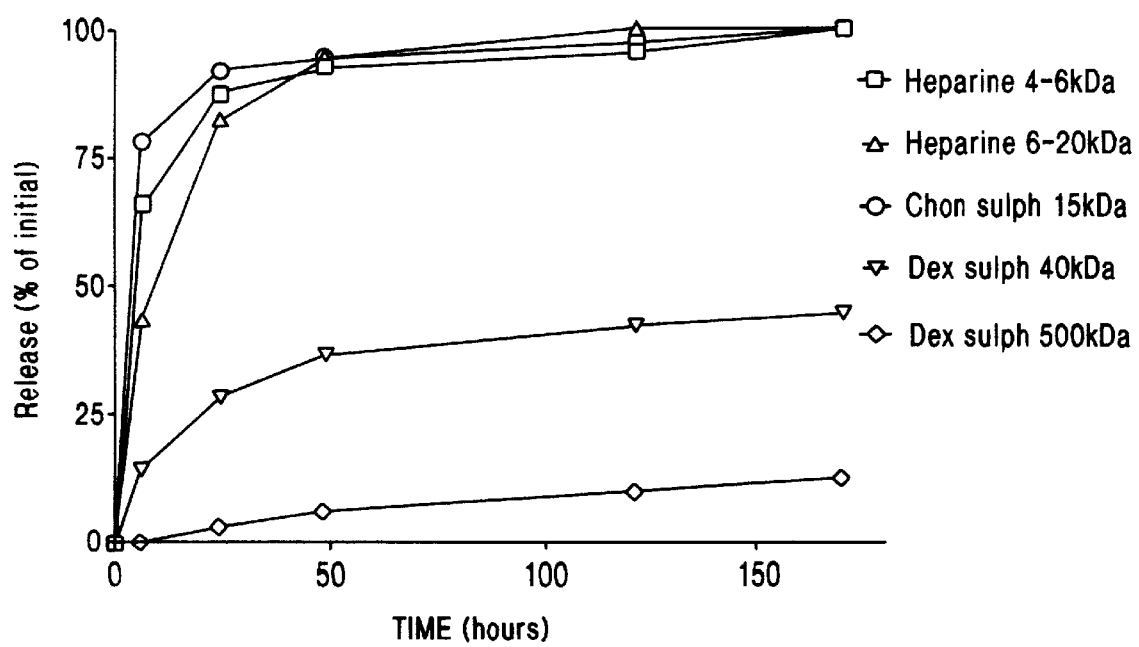
Figure 12A:
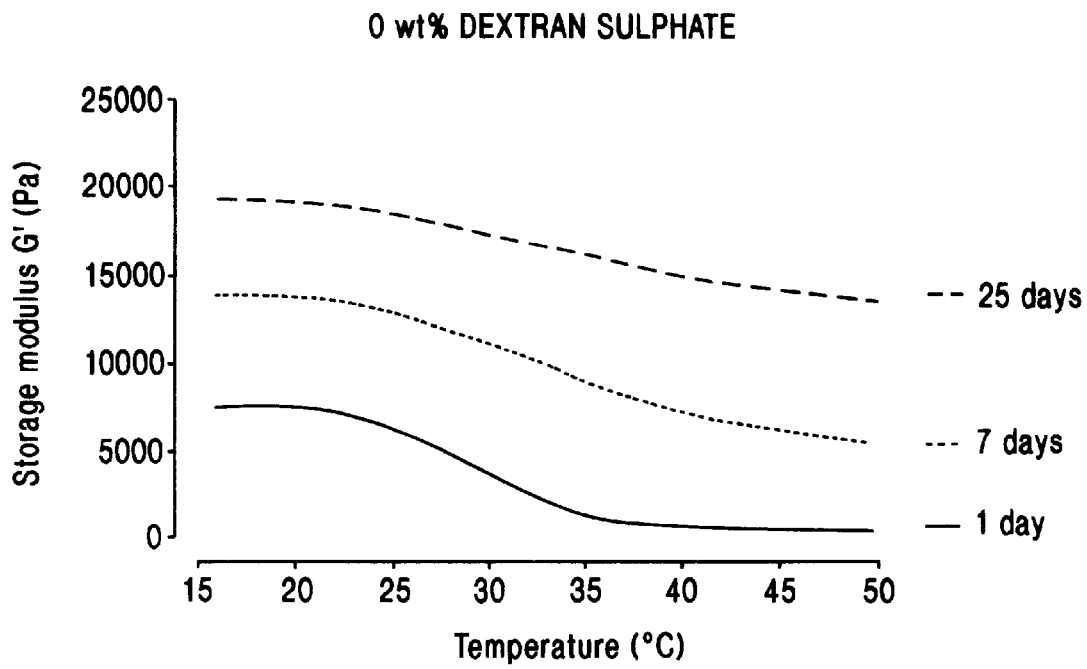
Figure 12B:
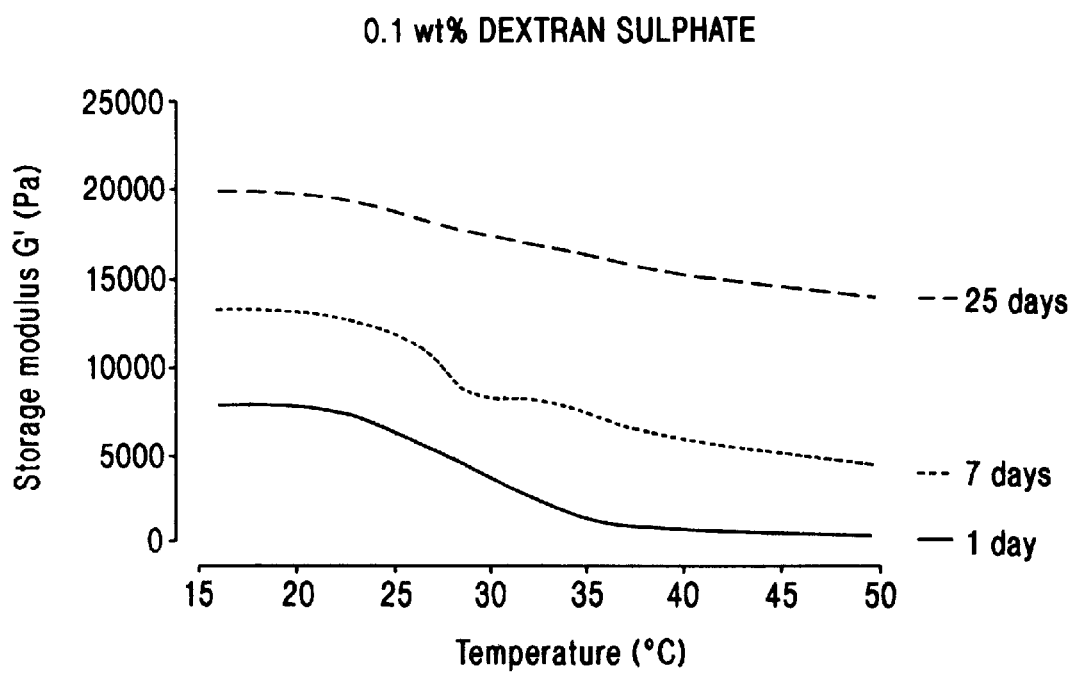
Figure 12C:
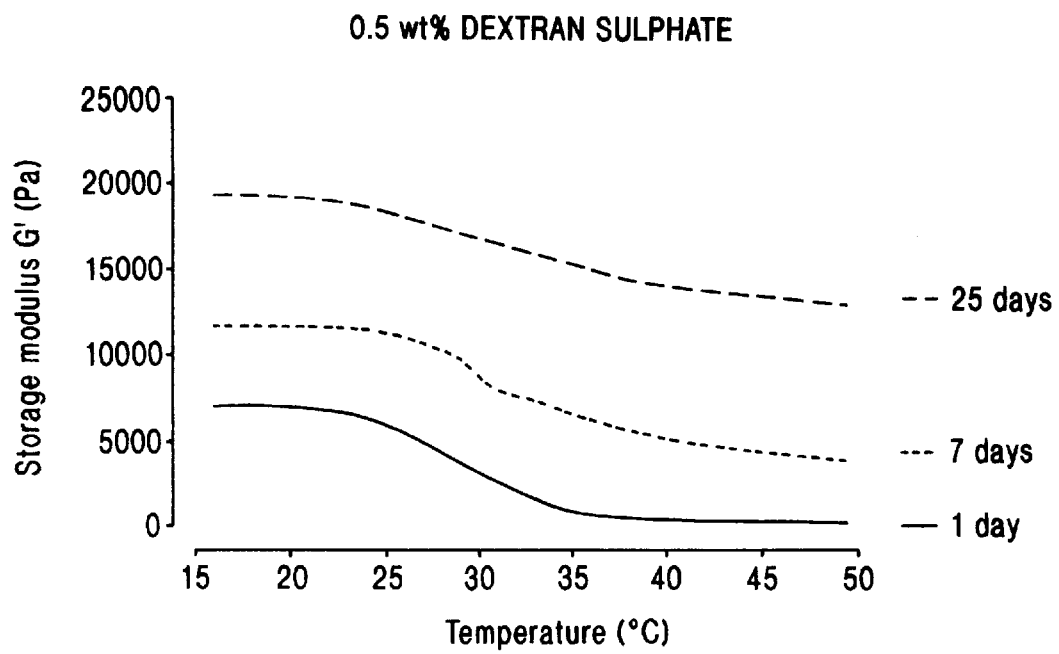
Figure 12D:
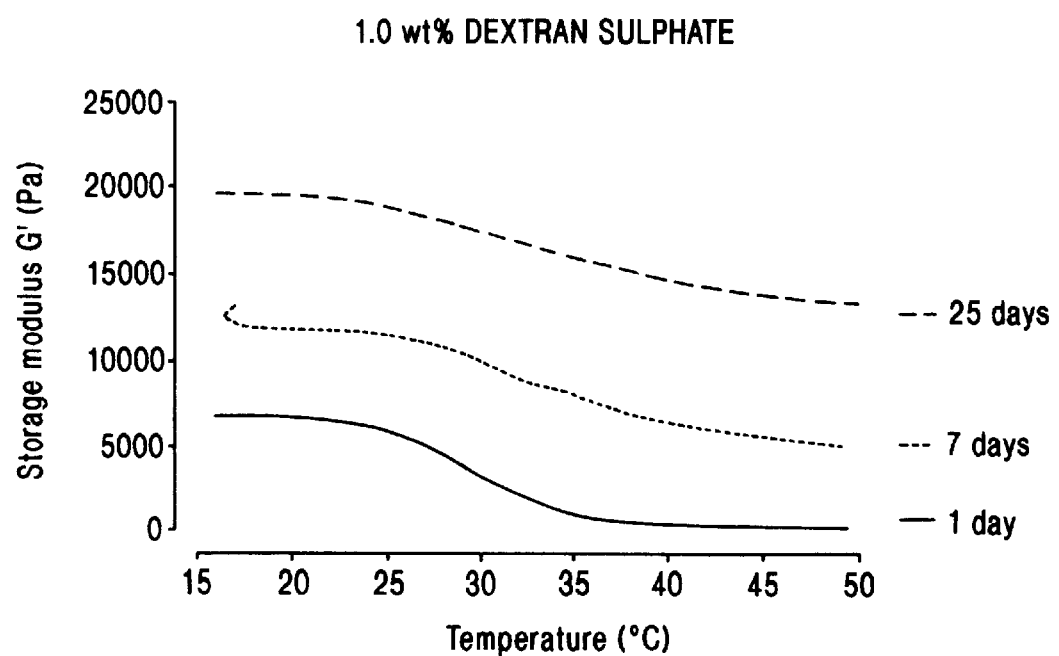
Figure 13A:
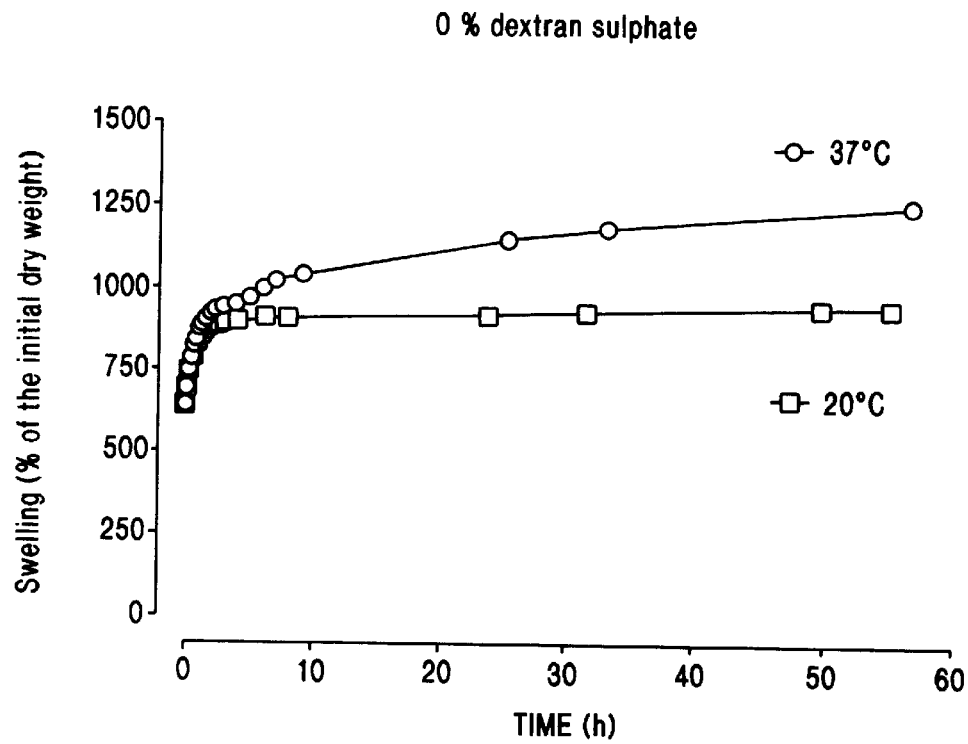
Figure 13B:
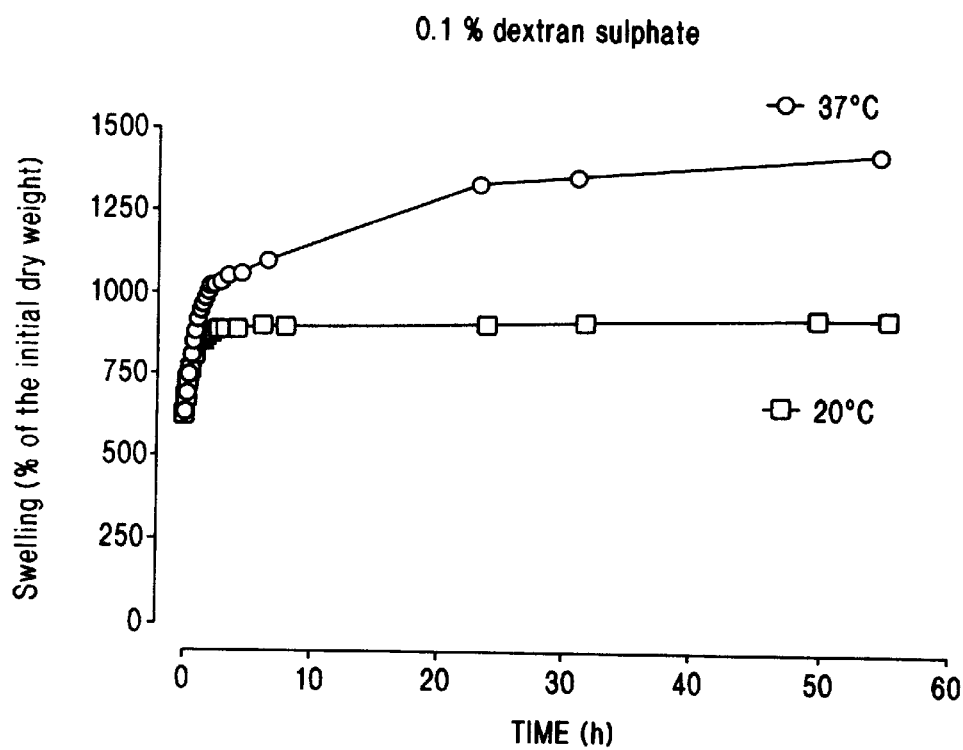
Figure 13C:
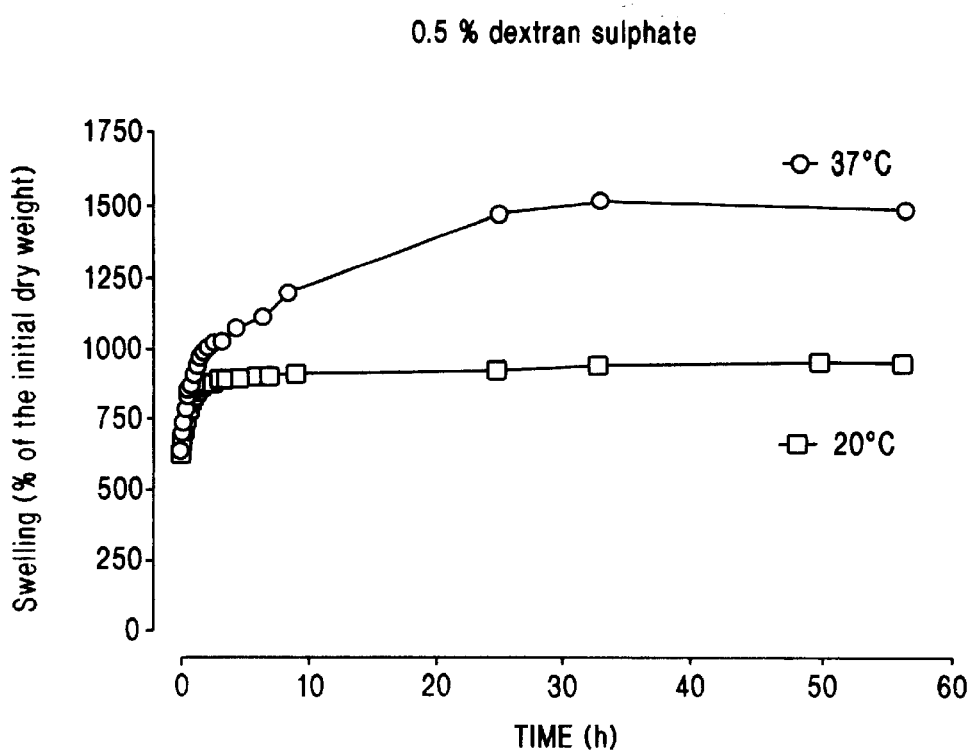
Figure 13D:
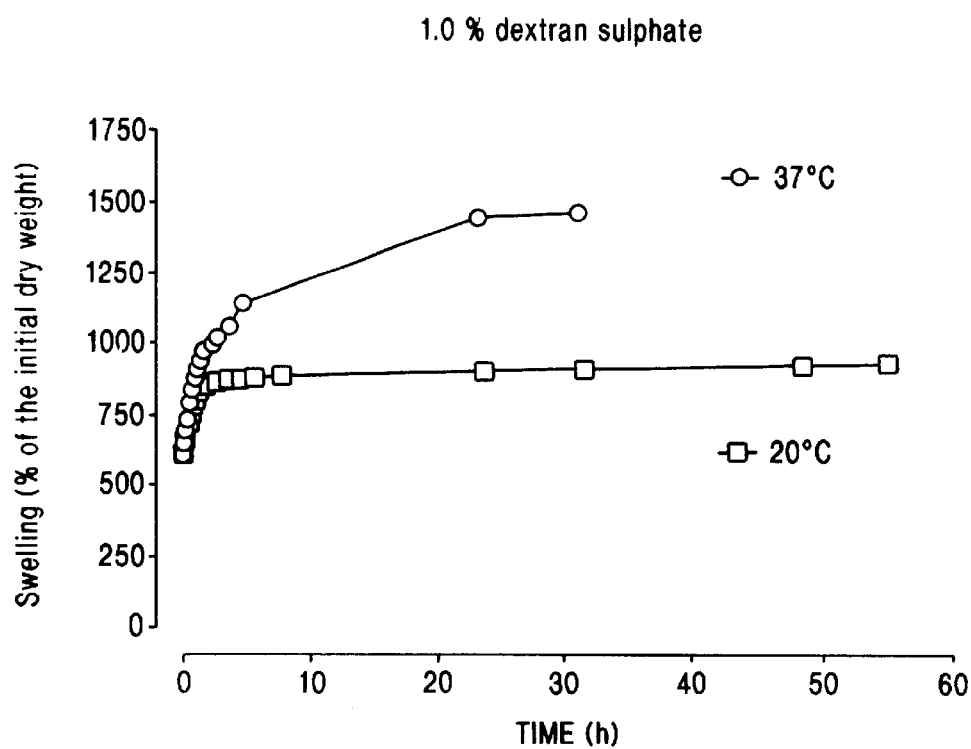

The release kinetics of polyanions from cross-linked gelatin hydrogels stored up to 2 months at 4° C. are evaluated. FIGS. 11 (A and B) shows the appearance of the polyanions in the extraction medium during the 7 day incubations. During incubations of 5 day old hydrogels (FIG. 11A), polyanions of low molecular weights (heparin and chondroitin sulphate) are completely released from the affinity matrix samples within a few hours. The majority (>80%) of dextran sulphate (MW: 40000) is released within 2 day incubations, this burst release is followed by a plateau release during the next 5 day incubation, leading to the complete polyanion release. By contrast, only about 30% of the hydrogel-incorporated dextran sulphate (MW: 400000–600000) is released during the 7 day incubations. A similar release experiment (FIG. 11B) performed 2 months after the hydrogel production showed similar patterns for polyanions of low molecular weights (heparin and chondroitin sulphate), but the released amounts of dextran sulphate (MW: 40000 and 400000–600000) are markedly decreased to about 44 and 10%, respectively. This example thus indicates that in order to use the affinity matrix as a reservoir for endogenous growth factors, polyanions of low molecular weight have to be cross-linked to the hydrogel matrix. Affinity matrices containing polyanions of high molecular weight (dextran sulphate MW 400000–600000) can be used without additional cross-linkage of the polyanions, since after the process of chemical cross-linking and physical structuring of the gelatin hydrogel matrix which takes about one week, only about 10% of the hydrogel matrix incorporated polyanion is released.

Example 10

Swelling and Visco-elastic Properties of the Dextran Sulphate-containing Cross-linked Gelatin Hydrogel Films Preparation of Dextran Sulphate-containing Affinity Matrices.

Gelatin type B (G-9382, lot 26H0347) from Sigma is prepared by alkaline treatment of bovine skin. The gel strength is 225 Bloom. The gelatin is sterilized by gamma-irradiation (0.6 Mrad) prior to use. Dextran (MW 70000) purchased from Pharmacia Fine Chemicals (Uppsala, Sweden) is dried at 80° C. on phosphorus pentoxide. Dextran dialdehydes (20% oxidized dextran) are prepared as described in example 1. Dextran sulphate (MW500000, sulphur content 17%) is obtained from Pharmacia Fine Chemicals (Upsala, Sweden). The hydrogels are prepared by physically (SIPN) entrapping dextran sulphate during the cross-linking of gelatin and dextran dialdehydes. The gelatin and dextran dialdehyde concentrations are 10 and 5%, respectively, and four concentrations of dextran sulphate (0, 0.1, 0.5 and 1wt %) are incorporated in the hydrogel matrix. The reaction is performed in an aqueous medium (phosphate buffer, pH 6.5). Both solutions are mixed and the final solutions are stirred at 40° C. for 1 minute. The 1 mm hydrogel films are prepared as described in example 1.

Visco-elastic and Swelling Measurements

The Theological measurements at oscillatory shear deformation on the hydrogel films are carried out with a CSL$^2$ Rheometer (TA Instruments) using parallel rough plates of 40 mm diameter and a plate-to-plate distance of 800 $\mu$m. The temperature dependence of the storage (elastic) modulus is determined by oscillatory shear deformation and temperature scan in the range from 16 to 50° C. (heating rate 1.75° C. min$^{-1}$) at constant frequency (1 Hz) and constant shear strain ($\gamma$=0.05, 1.8 mrad). The hydrogel formation (gelation) of dextran dialdehyde-gelatin aqueous solutions is governed by two strong interactions. One is associated with the chemical cross-linking of gelatin and dextran dialdehydes (gelatin-dextran chemical interaction) and the other is based on the ability of gelatin to form polymer 5 network structures that are stabilised by physical cross-linking (gelatin-gelatin physical structuring). The temperature scan of the hydrogel samples below and above the hydrogel melting point allows the evaluation of the respective contribution of the chemical and the physical cross-linking interactions in the hydrogel formation.

For measurements of the swelling properties, the cross-linked gelatin hydrogel films, prepared as described above, are stored at 4° C. for one week. Samples of hydrogels (1 mm thick discs, 32 mm in diameter) are weighed and then immersed in 80 ml of PBS buffer (pH 7.4) maintained at either 20° C. or 37° C. The immersion medium contains sodium azide. At particular time points, the hydrogels are removed from the immersion solution, and after quick blotting with filter paper, weighed. Each point presented in this study is the mean value of triplicate measurements.

Results are expressed as percentage of swelling (S %) and were calculated by using the following equation:

$$S\% = [(W_{ht} - W_{d0})/W_{d0}] * 100$$

where $W_{d0}$ is the weight of the dry gel at time 0 and $W_{ht}$ is the weight of the hydrated or swollen gel on time t. The swelling experiments are started by using a series of hydrated hydrogel samples: i.e. hydrogel samples with 15 wt % of polymer content and about 600 wt % of water content (percentage of swelling). Hydrated hydrogel samples are used because drying the samples prior to the start of the experiments causes supplementary matrix cross-linking and a concomitant decrease in the swelling capacities of the hydrogel films. For this reason, the dry weight of the hydrogel samples at time 0 ($W_{d0}$) is estimated by weighing another series of hydrogel samples taken from the same hydrogel films. At the end of the immersion incubations, the hydrogel samples are dried on phosphorus pentoxide and weighed again to evaluate the hydrogel sample final dry weight. The loss of hydrogel dry weight during the swelling experiment allows the calculation of a hydrogel solfraction and gelfraction. The solfraction is the fraction of the polymer lost during the hydrogel immersion incubation and the gelfraction is the remaining part of the polymer.

The Visco-elastic Properties of Cross-linked Gelatin Hydrogels Films Containing Physically Entrapped Dextran Sulphate The effect of increasing the storage time on the visco-elastic properties of the dextran sulphate-containing cross-linked gelatin hydrogel films is evaluated by rheological measurements. The hydrogel films containing four different concentrations of dextran sulphate (0, 0.1, 0.5 and 1%) are stored at 4° C. during 1 day, 7 and 25 days. The temperature dependence of the storage modulus (G') in function of hydrogel storage time is shown in FIG. 12. The cross-linked hydrogel films show a large increase in their strength with increasing storage time, most of the physical cross-linking occurred during the first day, while the chemical cross-linking is strongly improved with longer storage time. The hydrogels containing different amounts of dextran sulphate show almost identical curves. The storage modulus G' is not significantly modified by the addition of dextran sulphate (up to 1%), indicating neglectable influence of those concentrations of dextran sulphate on the visco-elastic properties of the hydrogel films.

Swelling Properties of Cross-linked Gelatin Hydrogels Containing Physically Entrapped Dextran Sulphate The water uptake of cross-linked gelatin hydrogel films containing increasing amount of dextran sulphate (0, 01, 0.5 and 1%) is evaluated after hydrogel PBS-immersion incubations at either 20° C. or 37° C. As seen in FIG. 13, at 20° C. hydrogel water uptake reaches a plateau after 3 hours of hydrogel immersion at a swelling percentage of about 900%. At 20° C., the plateau values are not changed by the presence of increasing amount of incorporated dextran sulphate. At 37° C., the plateau values are reached later (after about 24 h of hydrogel immersion) and are higher than those recorded at 20° C. Moreover, at 37° C., the plateau values are modified (increased) by the presence of dextran sulphate in the hydrogel matrix. The effect of the presence of increasing amount of dextran sulphate on the swelling properties at 37° C. is shown in FIG. 14. After one-day incubations, hydrogel films containing no dextran sulphate absorb water to about 1200%, those containing 0.1% dextran sulphate show more water uptake (to about 1400%) and those containing either 0.5 or 1% further absorb water to about 1500%. There is no further hydrogel water uptake by increasing the hydrogel dextran sulphate content from 0.5% to 1%. At the end of the swelling incubation time, hydrogel samples are dried and weighed and the final dry weights are compared with the initial dry weight in order to evaluate the hydrogel loss of weight during the incubation. Table 3 gives the gelfraction and the solfraction of the hydrogels of the different composition.

TABLE 3

| Incubation Temperature (°C.) | Hydrogel dextran sulphate content (wt %) | Gelfraction (%) | Solfraction (%) |
|---|---|---|---|
| 20 | 0.0 | 78 ± 1 | 22 ± 1 |
|  | 0.1 | 77 ± 0 | 23 ± 0 |
|  | 0.5 | 79 ± 0 | 21 ± 0 |
|  | 1.0 | 79 ± 1 | 21 ± 1 |
| 37 | 0.0 | 63 ± 1 | 37 ± 1 |
|  | 0.1 | 51 ± 9 | 49 ± 9 |
|  | 0.5 | 58 ± 3 | 42 ± 3 |
|  | 1.0 | 60 ± 4 | 40 ± 4 |

The solfractions that are find at 37° C. are higher than those found at 20° C., indicating that an increased fraction of the hydrogel components is released from the hydrogel samples during the incubations at 37° C. The gel- and sol-fraction of all gelatin hydrogels containing different concentrations of dextran sulphate are comparable.

The Theological measurements shown in this example thus further confirm that the process of chemical cross-linking and physical structuring of the dextran dialdehyde cross-linked gelatin hydrogel matrix does not occur instantaneously. Here again, important changes in the mechanical properties occur during the first week after the hydrogel production, thereafter, the elastic properties are stabilised. The present rheological study shows that the incorporation of dextran sulphate (up to 1%) into the hydrogel matrix does not modify the elastic properties of the hydrogel films.

The swelling experiments show that in the presence or the absence of dextran sulphate in the cross-linked gelatin hydrogel films, hydrogel water uptake is higher at 37° C. than at 20° C. Above the melting point of gelatin (at 37° C.), the physical structuring of the hydrogel is destroyed leading to hydrogels with a lower density and causing better swellability of the hydrogel. When the physical structuring of the hydrogels are destroyed (at 37° C.), the presence of dextran sulphate contributes to increase the hydrogel water uptake capacities. At 37° C., the solfractions of the hydrogels are increased indicating an additional lost of polymer components at this incubation temperature. This additional hydrogel component lost can be the consequence of the release of the fraction of gelatin not chemically cross-linked, since in these conditions, the temperature (37° C.) of the hydrogel immersion incubations is above the gelatin melting point. The presence of dextran sulphate in the hydrogel does not interfere with this process.

Example 12

In Vivo Biocompatibility of Cross-linked Gelatin Hydrogels and Dextran Sulphate Containing Cross-linked Gelatin Hydrogels During Wound Healing in Pig GDP Film Production In order to obtain dextran dialdehyde cross-linked gelatin hydrogel (GDP) and dextran sulphate-containing GDP films with more appropriate mechanical properties, the films are produced about 3 weeks before the start of the experiment.

One mm thick GDP films were prepared between 2 glass plates by mixing gelatine (10%, final concentration) and dextran dialdehydes (5%, final concentration), both prepared in PBS and warmed at 40° C. After about one hour at room temperature, the GDP films were stored for about three weeks at 4° C. Two hours before use, the films were rewarmed at room temperature. Dextran sulphate-containing GDP films are prepared similarly to GDP films, except that dextran sulphate (MW 400000–600000) is added to the dextran dialdehyde solution before mixing with gelatin (SIPN) in order to obtain a final concentration of dextran sulphate of 0.5%.

Gelatin: N°4, 4488AF2 144, from Sanofi, irradiated 0.6 Mrad in May 1995, endotoxin contents: 1.405 EU/g, 10%, final concentration, with the following characteristics: 254 bloom pH 4.97, PI 7.28, obtained from bovine acid-cured tissue, after a second acid extraction (4–5 h at 55° C.), the first extraction is performed at 50° C. after a pre-treatment at 40° C. and at pH 1–2 for 24 hours.

Dextranox: (20% oxidation, 5% final concentration, filtrated on 0.22 µm, endotoxin contents: 0.720 EU/g with a clinical grade dextran from ICN Biomedicals Inc Aurora, Ohio (MW 60000–90000, lot N° 59170), endotoxin contents: 1.700 EU/g.

Dextran sodium sulphate (MW 400000–600000), from ICN Biomedicals Inc Aurora, Ohio, lot N° 64914.

The Porcine Model

In this example a pig model is conducted in order to further characterize and confirm the biocompatibility of dextran dialdehyde cross-linked gelatin hydrogel (GDP) dressing when placed in a full-thickness wound environment. The biocompatibility of GDP is evaluated, in comparison with two largely used dressings, the hydrocolloid dressing DuoDERM and the occlusive dressing Tegaderm, by characterization of the intensity and/or time duration of the inflammatory reaction during wound healing. A pilot study is also performed on 4 wounds to evaluate the biocompatibility of 0.5% dextran sulphate-containing GDP (affinity matrix).

A porcine model is chosen because of the morphological and functional similarities between pig and human skin. An unsutured full-thickness cutaneous wound model (2 cm×2 cm square wounds) is chosen because it is easily reproducible, and provides sufficient wound tissue to quantify connective tissue deposition (e.g. collagen) and cellular changes during wound healing. Moreover, with full-thickness excisional wounds, one can make reasonable observations on wound resurfacing by contraction and re-epithelialization.

Castrated male Belgian Landrace pig, approximately 4 months old at the time of wounding, weighing 50 kg, are housed in controlled temperature (20° C.) and fed a maintenance diet for sows ad libitum. The pig receives 8 cc penicillin/streptomycin as presurgery treatment. Before surgery, the pig receives stresnil (1 ml/20 kg), and the anaesthesia is induced by the inhalation of halothane (4%) administered together with oxygen and nitrous oxide both at 2 l/min. After endotracheal intubation, the pig is maintained anaesthetized by the inhalation of halothane (1–2%) administered together with oxygen and nitrous oxide both at 2 l/min. Premature recovery from anaesthesia is controlled by intravenous injection of Diprivan (Propofol) until appropriate anaesthesia is obtained.

The skin of the back and sides is surgically prepared by shaving, washing with Neo-Sabimol and water, and disinfecting with 70% ethanol containing Hibithane. To reduce anatomical variation in the wound healing response, 24 full-thickness square wounds (2 cm×2 cm) are made 5 cm apart in the area located between the shoulder and thigh within minimum 2.5 cm and maximum 12 cm from the pig backbone. The skin is excised to the fascia with a scalpel, and care is taken to avoid muscle excision.

Immediately after surgery, 4 wounds are untreated (controls), 8 wounds are treated with gelatine-dextranox polymer (3.5 cm×3.5 cm, placed over the wounds), 4 wounds are treated with gelatine-dextranox polymer (3.5 cm×3.5 cm, placed over the wounds) containing 0.5% dextran sulphate (MW: 400000–600000), and 8 wounds are treated with extra thin DuoDERM (5 cm×5 cm), a hydrocolloid dressing from Convatec. All the wounds are covered with Tegaderm, an occlusive dressing which provides for a moist environment, and which is obtained from 3M Medical products. Dressings are fixed with Fixomull stretch, from Beiersdorf, and Velpo bandages to prevent possible self-trauma to the wounds.

Evaluation of Wound Healing by Planimetry and Histology

Photographs of the wounds are taken and the edges of the wounds are traced on cellophane sheets to measure areas and perimeters of the wounds during wound healing. A public domain image processing and analysis program (NIH Image) for Macintosh computer is used for measurements of areas and perimeters of the wounds. This allows to evaluate quantitatively the wound resurfacing by measuring, from the digitized contours, the change in wound area for a given period of time due to either contraction or to both contraction and re-epithelialization, and calculate the average length of advance of the wound margin per day.

The rate of wound closure is evaluated by measuring the decrease of open wound area from the wounding time to the time of wound closure. The open wound area is given in percent of the initial wound area.

(Open wound area (cm$^2$) on day x/original wound area (cm$^2$) on day 0)×100

Wound contraction is a normal process whereby the wound margins are pulled to the centre of the wound. In our porcine model, the initial square shape of the wound is progressively modified by contraction. The edges of the initial square becomes concave. Edge movement is less pronounced in the dorso-ventral direction than in the head-tailed axis. The contribution of contraction to wound closure is evaluated by measuring the decrease in the area (expressed as percentage of the initial wound area) given by the sum of re-epithelialized area together with the open wound area.

[(open wound area (cm$^2$) on day x+re-epithelialized area on day x)/original wound area (cm$^2$) on day 0]×100

The radial progression (d) of the wound margin towards wound closure is given in cm/day.

$$d=[(A_1-A_2)/(P_1+P_2)]/T$$

Where:

$A_1$ is the area of the wound at a given $T_1$ time after wounding $A_2$ is the area of the wound at a given $T_2$ time after wounding $P_1$ is the perimeter of the wound at $T_1$ time after wounding $P_2$ is the perimeter of the wound at $T_2$ time after wounding T is the time given in days between the two wound healing evaluations. Since the dressings are not changed during this evaluation, $A_1$ and $P_1$ are the area and the perimeter of the wound at day 0, respectively.

In order to perform the histological evaluation of wound healing and the evaluation of the inflammatory response to the implant, full-thickness skin biopsies are harvested, under general anaesthesia, at days 5, 10, 15 and 23 after surgery. Ellipses are excised to include the surrounding intact skin and the whole wound. The biopsies are fixed in 4% paraformaldehyde for classical histological evaluation and picro-Sirius red staining (evaluation of the collagen fiber deposition and maturation with the help of polarized light microscopy). The deep and large wounds produced by biopsy removal are partially sutured and covered with Tegaderm.

For classical histological evaluation, the paraformaldehyde fixed sections are stained either with hematoxylin and eosin, trichrome stain, periodic acid Schiff (PAS) stain, or Perls' Prussian blue reaction.

Body Weight and Animal Behaviour

The body weight of the pig is 50 kg the day of wounding. The body weight is not modified day 5 after surgery, but increases to 60 and 65 kg, day 10 and 15 after surgery, respectively, indicating that, although 6 large biopsies are harvested at each time of wound healing evaluation (days 5 and 10 after wounding), the pig is not too much affected by the 3 first repetitive anaesthesia and surgical procedures. Day 23 after surgery, the body weight still remains that of day 15, indicating that finally the harvesting of a total 18 large biopsies might stop the increase in body weight of the animal. The days after each surgical procedure, the behaviour of the pig had grossly returned to normal (normal activity, eating, drinking, etc).

Kinetics of Wound Closure

Figure 15A:
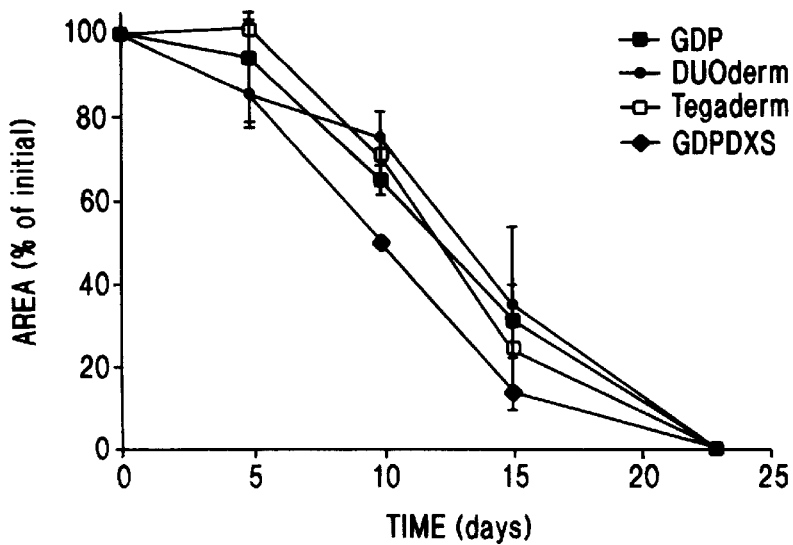
Figure 15B:
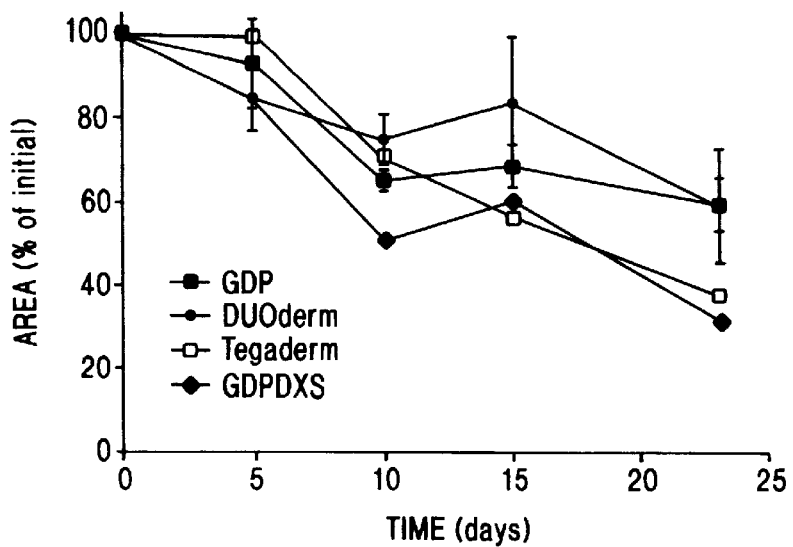
Figure 16A:
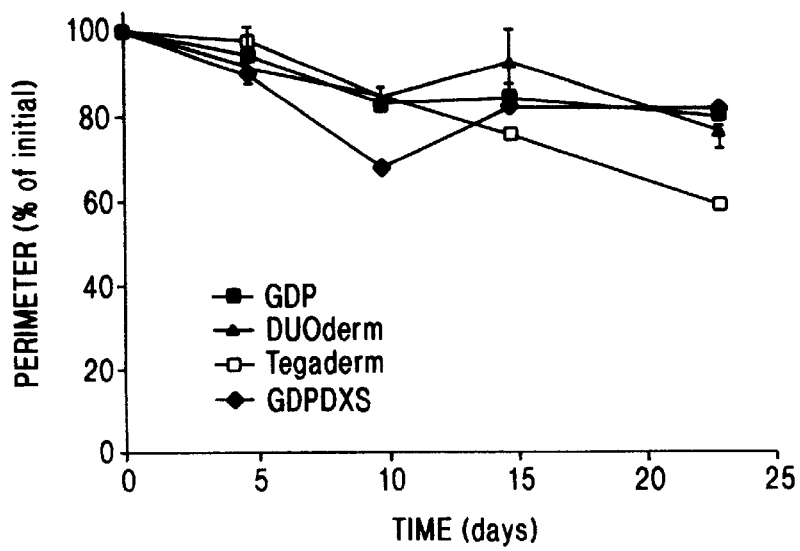
Figure 16B:
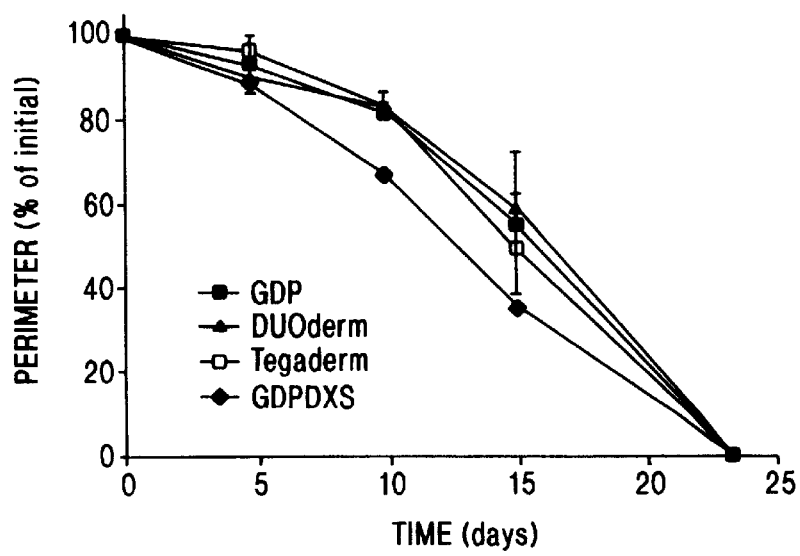
Figure 17:
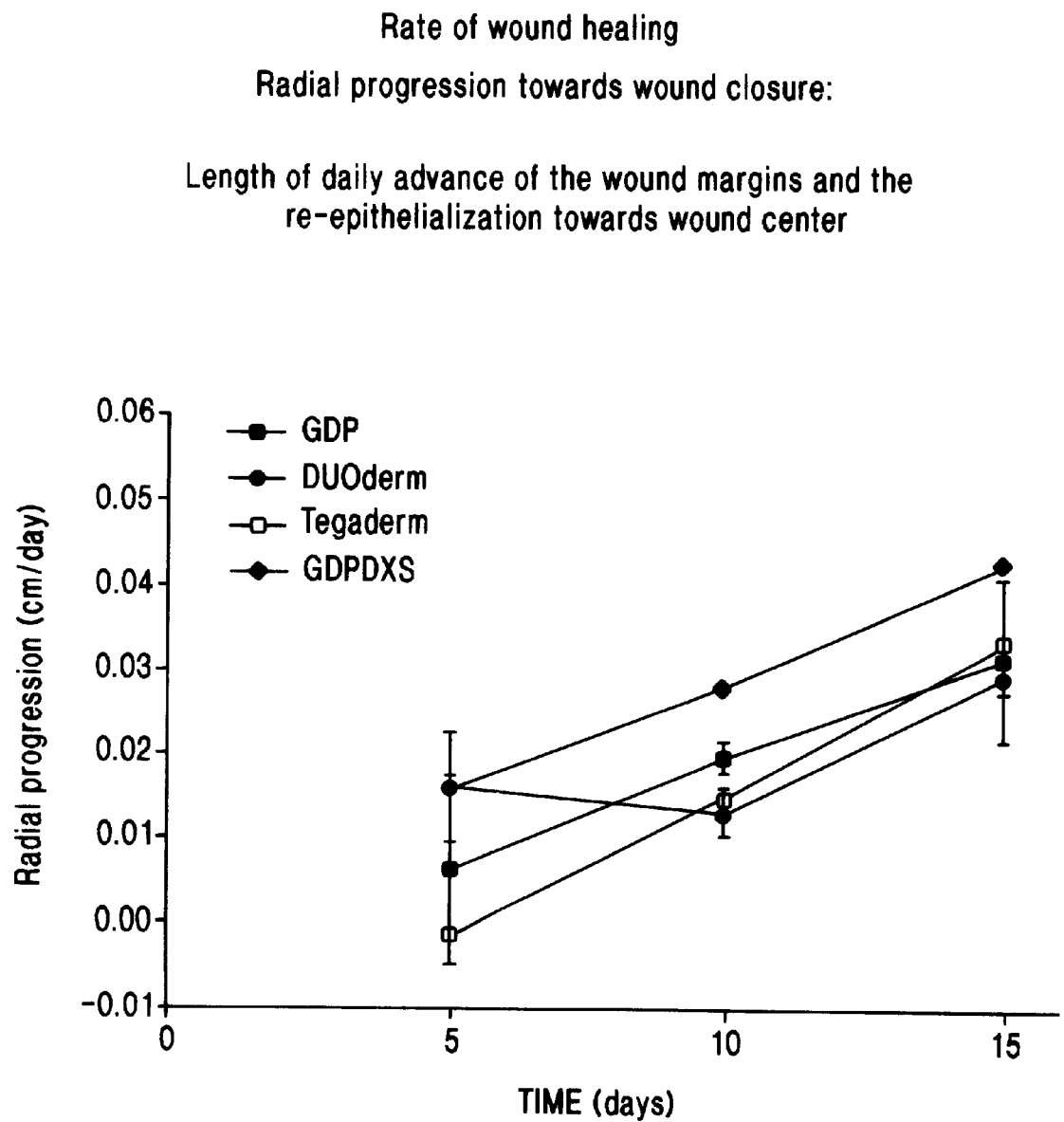

The days of biopsy removals (days 5, 10, 15 and 23), the rates of wound closure, due to both contraction and re-epithelialization, are quantitatively evaluated by planimetric measurements of the remaining open wound areas. Declining areas of the wounds plotted against the time past wounding are shown in FIG. 15a. The kinetics of wound closure were found to be similar for GDP, Duoderm and Tegaderm treatments, indicating that GDP treatment is at least as good as two of the best and largely used dressings. Wounds treated with 0.5% dextran sulphate-containing GDP always appear in a more advanced stage of healing. For dextran sulphate-containing GDP-treated wounds as well as for Tegaderm-treated wounds, only one wound per treatment is evaluated, at each time of biopsy removals. With all treatments, the wounds are closed at day 23 after surgery. At this time, contraction (movement of the intact skin at the wound edges towards the center of the wounds) accounts for about 40% of wound closure for GDP and Duoderm treated wounds, and for about 60% for dextran sulphate-containing GDP and Tegaderm treated wounds (FIG. 15b). As can be seen in FIG. 16a, the reduction of the perimeters by contraction is lower than the reduction of wound areas (FIG. 15b). By using the open wound areas values from FIG. 15a and the open wound perimeters of FIG. 16b, we calculate the length of daily advance of the wound margins (contraction+ re-epithelialization) towards the wound center. As can be seen in FIG. 17, the radial progression towards wound closure is similar for three treatments (GDP, Tegaderm and Duoderm) indicating again that GDP is a dressing at least as good as Tegaderm or Duoderm, and certainly does not interfere negatively with wound healing. The radial progression of the wounds treated with dextran sulphate-containing GDP is always higher than those of GDP-, Tegaderm- and Duoderm-treated wounds, indicating that dextran sulphate-containing GDP is a good candidate to accelerate wound healing.

Wound Healing

According to our macroscopic evaluations, GDP does not interfere negatively with wound healing in pig, the healing of GDP-treated wounds is comparable to the healing of wounds treated with two good dressings (Duoderm and Tegaderm). The healing of the wounds treated with dextran sulphate-containing GDP is always in a more advanced stage than the healing of GDP, Tegaderm and Duoderm-treated wounds, indicating that dextran sulphate-containing GDP is a good candidate to accelerate wound healing.

Histological evaluations of wound biopsies show that inflammatory cells, inflammatory foci and granulomas are always, and by far, more abundant in the granulation and the cellular scar tissues of Duoderm-treated wounds. Both cavities containing particles of Duoderm material and granulomas with numerous foreign-body giant cells are characteristic for the scar tissue of Duoderm-treated wounds. Inflammatory foci are also present in the granulation and the scar tissues of dextran sulphate-containing GDP-, GDP- and Tegaderm-treated wounds, but they are less abundant than in Duoderm-treated wounds and contain less foamy macrophages and foreign-body giant cells. Abundance of inflammatory foci is: Duoderm>GDP, dextran sulphate GDP, Tegaderm. In conclusion, a weak to moderate foreign body reaction is observed with Dextran sulfate-containing GDP- and GDP-treated wounds. By contrast, a strong foreign body reaction is seen in the Duoderm-treated wounds. GDP and dextran sulphate-containing GDP can thus be considered as biocompatible dressings. In this example, dextran sulphate containing GDP-treated wounds re-epithelialize faster than DuoDERM and Tegaderm treated wounds indicating that dextran sulphate-containing GDP is a better candidate to accelerate wound healing. Moreover, on the basis of the collagen organisation in the scar tissue and the presence of a basement membrane under the new epithelium, dextran sulfate-containing GDP-treated wounds are always found to be in a more advanced stage of wound haling.

What is claimed is:

1. A medicament containing a biopolymer matrix comprising gelatin cross-linked with an oxidized polysaccharide and wherein a polysulfated polysaccharide with a MW greater than 30,000 kDa is mechanically entrapped during the formation of said matrix, thereby forming a semi-interpenetrating polymer network.

2. A medicament containing a biopolymer matrix of claim 1 wherein said oxidized polysaccharide is an oxidized dextran or an oxidized xanthan.

3. A medicament containing a biopolymer matrix of claim 1 wherein additional compounds are attached to and/or incorporated into said matrix, with said additional compounds being selected from the group consisting a biocompatible polyanion which has the capacity to bind heparin-binding growth factors;

a proteoglycan containing glycosaminoglycan chains capable of binding to heparin-binding growth factors;

a functional analog of heparin which can bind or stabilize heparin-binding growth factors and a monoclonal or polyclonal antibody or a microprotein obtainable by phage display that have a high and selective affinity for molecular factors that can modulate the wound healing process.

4. A medicament containing a biopolymer of claim 1 wherein said matrix is in the form of a hydrated film.

5. A medicament containing a biopolymer of claim 1 wherein said matrix is in the form of a hydrated or dry foam.

6. A medicament containing a biopolymer of claim 1 wherein said matrix is in the form of dry fibers, which may be fabricated into a woven or non-woven tissue.

7. A medicament containing a biopolymer matrix of claim 1 wherein said matrix is in the form of hydrated or dry micro beads.

8. A medicament containing a biopolymer matrix of claim 1 wherein said matrix is in the form of a dry powder.

9. A medicament containing a biopolymer matrix of claim 1 into which a therapeutically effective amount of a drug is non-covalently incorporated.

10. A medicament containing a biopolymer matrix of claim 1 into which a therapeutically effective amount of a wound healing-stimulating drug is incorporated.

11. A medicament containing a biopolymer matrix of claim 3 wherein at least one of the additional compounds is selected from the group consisting of EGF-like factors, FGF-like factors, TGF-$\beta$-factors, IGF-like factors, PDGF-like factors, VEGF-like factors, keratinocyte cell lysate and purified keratinocyte lysate.

12. A medicament containing a biopolymer matrix of claim 3 wherein at least one of the compounds is an antiseptic.

13. A medicament containing a biopolymer of claim 1 in the form of a wound dressing and/or controlled release device.

14. A medicament of claim 13 in the form of a controlled or slow release for transdermal drug delivery.

15. A controlled or slow release device of claim 14 comprising micro particles loaded with a drug which can be injected intravenously, subcutaneously or intramuscularly.

16. A controlled or slow release device of claim 14 comprising micro particles loaded with a vaccine which can be injected intravenously, subcutaneously or intramuscularly.

17. A method of treating skin wounds or dermatological disorders of warm-blooded animals comprising applying to skin wounds on the skin of warm-blooded animals a medicament of claim 10.

* * * * *